US009734779B2

(12) United States Patent
Forutanpour et al.

(10) Patent No.: US 9,734,779 B2
(45) Date of Patent: Aug. 15, 2017

(54) EFFICIENT OPERATION OF WEARABLE DISPLAYS

(71) Applicant: QUALCOMM Incorporated, San Diego, CA (US)

(72) Inventors: Babak Forutanpour, Carlsbad, CA (US); William Thomas Frantz, San Diego, CA (US); Daniel Scott Baker, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 29 days.

(21) Appl. No.: 14/620,551

(22) Filed: Feb. 12, 2015

(65) Prior Publication Data

US 2016/0240154 A1 Aug. 18, 2016

(51) Int. Cl.
*G09G 3/36* (2006.01)
*G06F 1/16* (2006.01)
(Continued)

(52) U.S. Cl.
CPC .......... *G09G 3/3644* (2013.01); *G06F 1/163* (2013.01); *G06F 1/1641* (2013.01); *G06F 1/1652* (2013.01); *G06F 1/3218* (2013.01); *G06F 1/3265* (2013.01); *G06F 3/017* (2013.01); *G06F 3/044* (2013.01); *G06F 3/0412* (2013.01);
(Continued)

(58) Field of Classification Search
CPC .... G06F 3/1423; G06F 3/1431; G06F 3/1438; G09G 2340/0421
See application file for complete search history.

(56) References Cited

U.S. PATENT DOCUMENTS 7,081,870 B2   7/2006  Bronson
8,097,926 B2   1/2012  De Graff et al.
(Continued)

FOREIGN PATENT DOCUMENTS

EP         2717119 A1      4/2014
WO    WO-2014175513 A1    10/2014

OTHER PUBLICATIONS

International Search Report and Written Opinion—PCT/US2015/066441 ISA/EPO—Mar. 31, 2016.
(Continued)

*Primary Examiner* — Ricardo L Osorio

(57) ABSTRACT

This disclosure provides systems, methods, and apparatus, including computer programs encoded on computer storage media, for displaying information in various display regions within wearable display devices in a manner that enhances user experience and extends battery life. The wearable display devices may include a flexible display region and may be capable of operating in a wrinkled state. In some aspects, the wearable display devices may be capable of displaying images at different image qualities in the separate display regions. For example, in some implementations, wearable display devices include a first display region that has a higher pixel density than the second display region. In some aspects the wearable display devices may be configured to determine and/or select a display region in which specific image content is displayed. For example, text may be displayed region best suited to display text while video is displayed in region best suited to display video.

31 Claims, 33 Drawing Sheets

(51) Int. Cl.

| | | |
|---|---|---|
| *G06F 1/32* | (2006.01) | |
| *G06F 3/01* | (2006.01) | |
| *G09F 9/30* | (2006.01) | |
| *G06F 3/0484* | (2013.01) | |
| *G06F 3/041* | (2006.01) | |
| *G06F 3/044* | (2006.01) | |
| *G09G 3/20* | (2006.01) | |
| *A61B 5/117* | (2016.01) | |
| *G06F 21/62* | (2013.01) | |

(52) U.S. Cl.
CPC .......... *G06F 3/04842* (2013.01); *G09F 9/301* (2013.01); *G09G 3/2003* (2013.01); *A61B 5/117* (2013.01); *G06F 21/6245* (2013.01); *G06F 2200/1637* (2013.01); *G06F 2203/04102* (2013.01); *G06F 2203/04803* (2013.01); *G09G 2310/04* (2013.01); *Y02B 60/1242* (2013.01)

(56) References Cited

U.S. PATENT DOCUMENTS

| | | | |
|---|---|---|---|
| 8,277,052 B2 | 10/2012 | Gatley et al. | |
| 8,389,862 B2 | 3/2013 | Arora | |
| 8,638,311 B2 | 1/2014 | Kang et al. | |
| 8,811,951 B1 | 8/2014 | Faaborg et al. | |
| 8,886,334 B2 | 11/2014 | Ghaffari | |
| 9,097,891 B2* | 8/2015 | Border | G02B 27/0093 |
| 9,159,635 B2 | 10/2015 | Elolampi et al. | |
| 2011/0310094 A1* | 12/2011 | Park | G06F 1/1626 |
| | | | 345/419 |
| 2012/0169714 A1* | 7/2012 | Hsu | G02B 27/26 |
| | | | 345/419 |
| 2012/0306910 A1 | 12/2012 | Kim et al. | |
| 2013/0069969 A1 | 3/2013 | Chang et al. | |
| 2013/0215011 A1 | 8/2013 | Ke | |
| 2013/0222270 A1 | 8/2013 | Winkler et al. | |
| 2013/0222271 A1 | 8/2013 | Alberth et al. | |
| 2013/0222354 A1 | 8/2013 | Koivunen | |
| 2013/0265262 A1* | 10/2013 | Jung | G06F 3/041 |
| | | | 345/173 |
| 2013/0271350 A1 | 10/2013 | Lyons | |
| 2013/0281164 A1 | 10/2013 | Alameh et al. | |
| 2013/0342439 A1 | 12/2013 | Kwack et al. | |
| 2014/0049463 A1 | 2/2014 | Seo et al. | |
| 2014/0071043 A1 | 3/2014 | Jung et al. | |
| 2014/0098095 A1* | 4/2014 | Lee | G06F 3/041 |
| | | | 345/420 |
| 2014/0139404 A1* | 5/2014 | Takeda | G02B 27/0172 |
| | | | 345/8 |
| 2014/0152553 A1* | 6/2014 | Cha | G06F 3/013 |
| | | | 345/156 |
| 2014/0159862 A1 | 6/2014 | Yang et al. | |
| 2014/0191926 A1 | 7/2014 | Mathew et al. | |
| 2014/0232620 A1* | 8/2014 | Fujigaki | G02B 27/017 |
| | | | 345/8 |
| 2015/0049120 A1* | 2/2015 | He | G02B 27/01 |
| | | | 345/660 |
| 2015/0084857 A1* | 3/2015 | Kimura | G06F 3/03 |
| | | | 345/156 |
| 2015/0113473 A1* | 4/2015 | Otsuka | G06F 1/163 |
| | | | 715/781 |
| 2015/0145839 A1* | 5/2015 | Hack | G09G 3/3208 |
| | | | 345/207 |
| 2015/0150505 A1 | 6/2015 | Kaskoun et al. | |
| 2015/0154936 A1* | 6/2015 | Lee | G09G 5/006 |
| | | | 345/173 |
| 2015/0193102 A1* | 7/2015 | Lanier | G06F 3/017 |
| | | | 715/746 |
| 2015/0261046 A1* | 9/2015 | Miki | G02F 1/134309 |
| | | | 349/42 |
| 2015/0355677 A1 | 12/2015 | Breedvelt-Schouten et al. | |
| 2015/0373831 A1 | 12/2015 | Rogers et al. | |
| 2015/0378662 A1* | 12/2015 | Wan | G06F 3/1423 |
| | | | 345/156 |
| 2016/0041581 A1 | 2/2016 | Piccionelli et al. | |
| 2016/0054799 A1 | 2/2016 | Levesque et al. | |
| 2016/0239091 A1 | 8/2016 | Forutanpour | |
| 2016/0239190 A1 | 8/2016 | Forutanpour | |
| 2016/0299570 A1 | 10/2016 | Davydov | |

OTHER PUBLICATIONS

Cao H., et al., "Enhancing Privacy in Public Spaces Through Crossmodal Displays", Social Science Computer Review, vol. 26, No. 1, Feb. 1, 2008, XP055333155, pp. 87-102.

* cited by examiner

EFFICIENT OPERATION OF WEARABLE DISPLAYS

TECHNICAL FIELD

This disclosure relates to wearable devices. More particularly, this disclosure is directed to devices, systems, and methods for displaying information in various display regions within wearable display devices in a manner that enhances user experience and extends battery life.

DESCRIPTION OF THE RELATED TECHNOLOGY

Mobile and/or portable electronic devices with touch screen displays have become ubiquitous. Screen sizes of such devices have increased over time and flexible displays can become widely available. Some display devices are available in a wearable form or can be adapted to a wearable form, in which the display device can be releasably attached to a user's wrist, forearm, or the like. As screen flexibility and durability increases display devices which are wearable and highly-flexible may become more common. Power consumption of such devices will be an important consideration, as larger displays will require more power. As such, a need exists for devices, systems, and methods for displaying content in a user friendly and energy efficient manner.

SUMMARY

The systems, methods, and devices of this disclosure each have several innovative aspects, no single one of which is solely responsible for the desirable attributes disclosed herein.

In some aspects, a wearable display device includes a display. Driver circuitry may be electrical communication with the display. The driver circuitry may be configured to drive a first region of the display at a first image quality and a second region of the display at a second image quality different than the first quality. The device may include a processor. The processor may be capable of selecting a region of the display in which image data will be displayed. The processor may be capable of directing the driver circuitry to display image data in the selected region of the display. The selection of the region of the display in which image data will be displayed may be based at least in part on one or more of the following: a content type associated with the image data, an image format associated with the image data, a priority associated with the image data, user preference associated with one or more user profiles, and biometric information indicative of a current user. In some aspects, the processor is capable of assigning an image quality for a region of the display. The image quality may be one or more of the following: color gamut, resolution, range of colors, frame rate, size and shape of the image, refresh rate, and the like.

In some aspects, a wearable display device having a display area having at least two sub-regions configured to display at least two different image qualities may be operated by a method including receiving a command to display image content, selecting an appropriate sub-region of the display area for displaying the content, and displaying the content in the selected sub-region of the display area. In some aspects, a command is received from a software application. The software application may have a priority level associated with it and the selection of the appropriate sub-region of the display area may be based at least in part on the priority level. In some aspects, selecting the appropriate sub-region is based at least in part on information relating to the usage history of the software application. In some aspects, selecting the appropriate sub-region is based at least in part on remaining battery life of the wearable display device.

In some aspects, a wearable display device includes a display area. The display area may include at least a first display region and a second display region. Driver circuitry may be in electrical communication with the first display region and the second display region. The driver circuitry may be capable of displaying images within the first display region at a first image quality and displaying images within the second display region at a second image quality different than the first image quality. In some aspects, the first display region has a first pixel density and the second display region has a second pixel density different than the first pixel density. In some aspects, the driver circuitry is configured to drive the first display region at a first refresh rate and drive the second region at a second frame rate different than the first refresh rate. In some aspects, the first display region is capable of displaying a first color gamut and the second display region is capable of displaying a second color gamut different than the first color gamut.

In some aspects, a wearable electronic device includes a display. The display may include a first display region, a second display region, at least one sensor configured to provide information regarding the position of the first and second display regions, and a processor capable of selecting one of the first and second display regions to display first image data. The selection of a display region may be based at least in part on the position of the first and second display regions and a privacy level associated with the first image data. The processor may be capable of determining a privacy level associated with the first image data. The privacy level may be based at least in part on one or more of the following: content of the image data, source of the image data, and user selection.

In some aspects, a wearable electronic device includes a display capable of being operated in a curved state. The display may include a first display region, a second display region facing a different direction than the first display region when the display is in the curved state, and a processor. The processor may be capable of determining a privacy level of first image data to be displayed on the display and selecting one of the first and second display regions to display the image data based at least in part on the privacy level of the image data. The processor may be capable of comparing the privacy level of the first image data with the privacy level of second image data. In some aspects, the device includes at least one sensor configured to determine the orientation of the first and second display regions relative to the user. In some aspects, the display is flexible and the boundaries of the first and second display regions are determined at least on part on the orientation and deformation of the flexible display.

In some aspects, a method of displaying data on a wearable display includes designating a first display region and a second display region on the wearable display. The designation may be based at least in part on how the wearable display is oriented in space. The method may include determining a privacy level of image data to be displayed on the wearable display. The method may include displaying the image data on the first display region or the second display depending on the privacy level of the image data. In some aspects, the method includes determining how the wearable display is oriented in space. The method may include adjusting the boundaries of the first and second display regions based at least on part on the orientation of the wearable display.

In some aspects, a wearable electronic device includes a display, a plurality of sensors coupled to the display and configured to determine the state of the display, and a processor in electrical communication with the plurality of sensors. The processor may be configured to provide image data to the display. The processor may be capable of changing at least one characteristic of the image data provided to the display based at least in part on input received from the sensors. The changing at least one characteristic of the image data may include one or more of the following: resizing the image data, reshaping the image data, adjusting the resolution of the image data, and altering the brightness of the image data.

In some aspects, a method of displaying content on a flexible display includes displaying content on a flexible display, receiving electrical signals from one or more deformation sensors coupled to the flexible display, and altering the displayed content based at least in part on the received electrical signals. In some aspects, altering the displayed content includes increasing a font size of text within the displayed content.

In some aspects, a wearable electronic device includes a display. The display may include a plurality of ambient light sensors. A processor may be in electrical communication with the plurality of sensors. The processor may be configured to deactivate at least a portion of the display based at least in part on input received from the sensors. In some aspects, the display is capable of bending over at least a 180 degree arc. The display may be capable of being operated in a curved and/or wrinkled state.

Details of one or more implementations of the subject matter described in this disclosure are set forth in the accompanying drawings and the description below. Although the examples provided in this disclosure are primarily described in terms of wearable and flexible displays configured to be worn on a user's arm, the concepts provided herein may apply to other types of displays such as, for example, liquid crystal displays, organic light-emitting diode ("OLED") displays, and field emission displays. Other features, aspects, and advantages will become apparent from the description, the drawings, and the claims. Note that the relative dimensions of the following figures may not be drawn to scale.

It is to be understood that not necessarily all objects or advantages may be achieved in accordance with any particular implementation described herein. For example, aspects of certain implementations may be embodied or carried out in a manner that achieves or optimizes one advantage or group of advantages as taught herein without necessarily achieving other objects or advantages as may be taught or suggested by other implementations. Furthermore, the aspects and features described herein are not limited to any particular implementation of a wearable display device. Thus, wearable display devices may include more or less of the features and advantages herein described. Moreover, the various aspects and features from different implementations may be interchangeable. For example, the features of the wearable display devices in the various implementations may be switched between implementations.

BRIEF DESCRIPTION OF THE DRAWINGS

The following is a brief description of each of the drawings. From figure to figure, the same reference numerals are used to designate the same steps or components of the illustrated example implementations.

DETAILED DESCRIPTION

Figure 1:
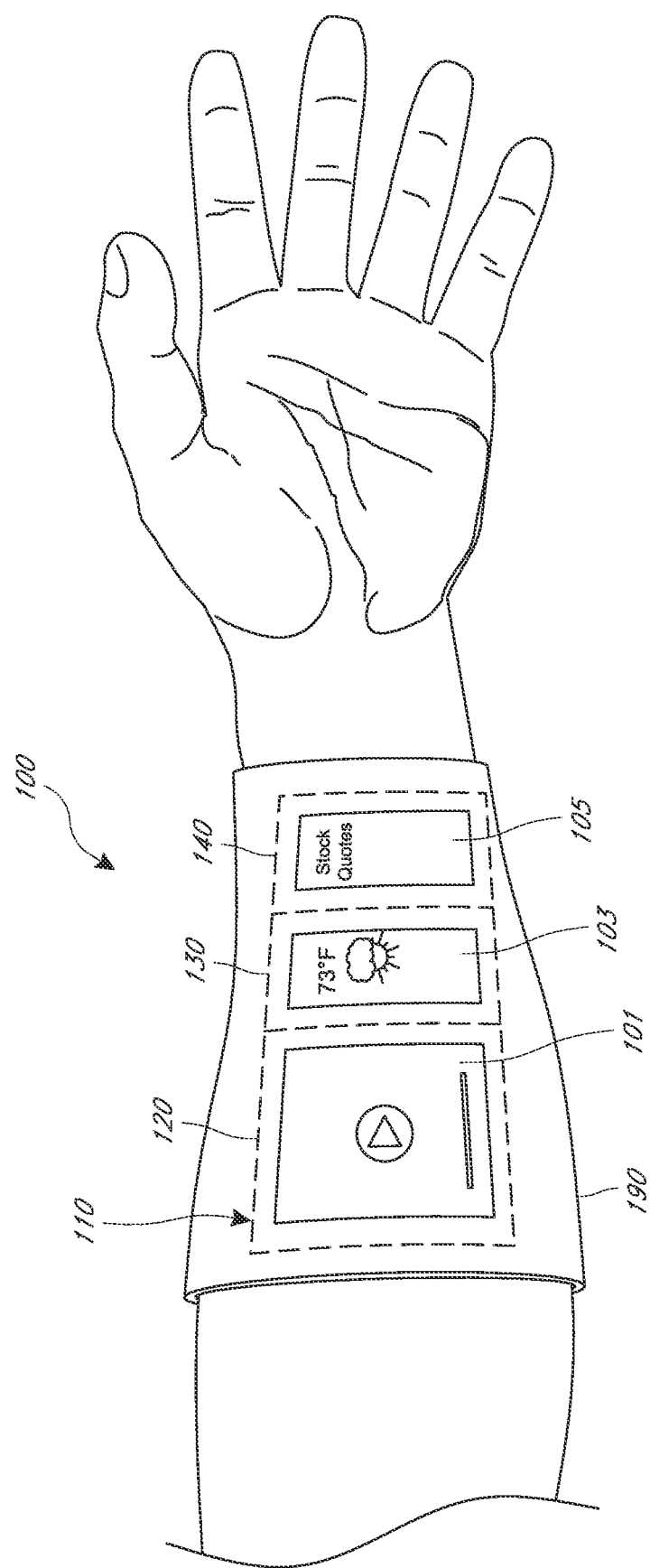
FIG. 1 illustrates an implementation of a large-format wearable display device.

The present disclosure provides systems, methods, and devices that may be used in connection with a wearable display. In some implementations, the device can be flexible. In some implementations, the device can be configured to be worn on or secured relative to a user's arm. For example, the device may include a sleeve, which may be semi-elastic and flexible. In other implementations, the display can be rigid or not substantially flexible. In some implementations the device includes one or more rigid sections which, may be planar or curved in a convex or concave manner.

In addition to a flexible display, the display device may include other components of varying flexibility. Such components may include one or more display screens, microphones, speakers, antennas, batteries, sensors, haptic feedback elements, processors, integrated circuits, input or output ports, and other components of a mobile computing device. Thus, the device may be a fully independent mobile computing device, while in other implementations the display device may be a companion device for use with a separate mobile computing device, such as a smartphone.

In some implementations, the device may have more than one display region, and be capable of displaying images at different image qualities in separate display regions. In other words, rather than having a display region capable of displaying images at a single image quality across the entire display, different display regions within the display can be capable to simultaneously display images at different image qualities within different display regions. In some implementations, a flexible display may be subdivided into two separate display regions, but in other implementations, a flexible display may be subdivided into more than two separate display regions.

These display regions may differ structurally from one another, or may be driven in such a manner that the displayed images are of different quality. In one implementation, a first display region may have a higher pixel density than a second display region, and the first display region may be capable of displaying higher resolution images than the second display region. In some implementations, for example, the device includes a first display region capable of displaying relatively complex image data, such as high-resolution images or video, and a second display region which is used to display relatively simple image data at a lower image quality, such as static text. In this way, information may be displayed from a multitude of sources and/or at a variety of different image qualities at appropriate display regions one of a display device.

The wearable display device may also be configured to determine and/or select a display region in which specific image content is displayed. For example, the wearable display device may display text in a display region that is best suited to display text and display video in a display region that is best suited to display video. In some implementations, the wearable display device may be configured to move the displayed content from a first display region to a second display region. For example, a video may be displayed in a first display region capable of displaying images at a high quality. When the video is paused, the device may move the video to a second display region having a second image quality that is less than the high image quality of the first display region. In this way, the content can be arranged and displayed in a more efficient manner.

The wearable display device may be capable of simultaneously running multiple applications or programs, or may be used in conjunction with a companion device with such capabilities. Each of these programs or applications may simultaneously display image data on respective portions of the wearable display device. The applications may be configured and/or assigned to display date in particular display regions. For example, the applications may display data in a particular display region depending on the type of image data that the application wishes to display. In some implementations, applications can be launched in a particular display region based on the content displayed by the applications. In some implementations, the display device can assign applications to specific display regions based on a display priority of the applications. For example, applications that will benefit from a higher quality display may launch in or be moved to display regions having appropriate display capabilities.

Techniques according to this disclosure may enable a wearable display device to selectively display public or private information based on the physical orientation of the wearable device with respect to the user. That is to say, the wearable computing device may be configured to display private information in areas within the display that are less likely or impossible to be viewed by someone other than the user. In some implementations, the wearable display device may display private information in areas that can only be seen by the user. In this way, individuals other than the user may be prevented from observing a user's private information displayed on the wearable display device.

The wearable display device may also be configured such that the device can determine the orientation of the device with respect to the user. That is to say, one or more sensors may enable the device to determine which portions of the device are facing towards a user's body and which portions are facing away from the user's body. In some implementations, the device may be configured to display more private information on display regions facing toward a user's body and less private information on display regions facing away from the user's body.

The wearable display device may also be configured such that the device can deactivate portions of the display that are obscured from a user's view. In this way, the device can conserve energy consumption. For example, the wearable display device may include one or more sensors configured to determine when portions of the display are covered by, for example, a shirt sleeve. These covered portions may be deactivated to conserve power consumption. In other implementations, the wearable display device can be configured to deactivate portions of the display that cannot be seen from a user's vantage point.

In some implementations, the wearable display device is configured to determine the status of the display and adjust the displayed content accordingly. For example, the device may include one or more deformation sensors configured to determine the physical deformation of the display area. In response to excessive wrinkling, for example, the displayed content may be moved to areas of the device that are less wrinkled and/or the relative size of the displayed content may be increased such that the readability and/or visualization of the displayed content is enhanced.

Particular implementations of the subject matter described in this disclosure can be implemented to realize one or more of the following potential advantages. By providing a device with varying display capabilities across a large-format display, the device may more efficiently render and display image data across a large screen. For example, different display regions in a display that are configured to display image data at different qualities may reduce the overall power consumption of the device. It may also reduce manufacturing costs, and may also reduce the required computing power required to drive the display. The various display regions may also enhance the user experience.

Flexible displays exist in the art. Such flexible displays may be available from, for example, Samsung, Sony, Sharp, Plastic Logic, and/or Arizona State University. These displays may be deformed, bent, curved, folded, wrinkled, unwrinkled, rolled, twisted, and/or stretched. As flexible display technology improves and prices decrease, new techniques of using and interacting with the flexible displays are needed to, for example, encourage widespread adaption of the technology. As such, one or more aspects of the present disclosure may prove especially useful as flexibility of displays continue to increase. However, it is to be understood that the implementations described herein may be implemented in devices which do not include flexible displays.

Other aspects of the disclosed devices may also be flexible. Flexible printed circuit boards, antennas, sensors, and/or batteries may also be included in the wearable display. In some implementations, the flexible, wearable, display devices may include some components or portions that are less flexible and more rigid than other components or portions. For example, more rigid components may be positioned relatively un-deformed orientations and more flexible components may be placed in areas that are subject to more bending and/or curvature. As such, portions of the display device along, for example, the top and bottom of the flexible display that extend parallel to the length of a user's arm may be less flexible than the portions that are generally perpendicular to the length of the arm. In this way, the use of more rigid components may be employed in a flexible display device. In some implementations, more rigid components may be housed in a separate companion component, such as a watch, bracelet, or smartphone.

FIG. 1 illustrates an implementation of a large-format wearable display device. As shown, the wearable display device 100 may be sized and shaped to snugly fit on a user's forearm between the wrist and the elbow. Thus, the wearable display device 100 may be flexible and/or somewhat elastic. However, as described above, one or more portions of the wearable display device 100 may be rigid. For example, in some implementations, the wearable display device 100 comprises a rigid display that is configured to fit around at least a portion of a user's arm in a bent or curved state, or a display with multiple rigid sections which can be moved independent of one another to allow the display to fit around at least a portion of a user's arm in a bent or curved state. In some implementations, the wearable display device 100 may include a supporting member 190, such as a band, strap, or sleeve which supports a display area 110 configured to display image data, such as text, images, social media, video, user interface elements, and/or other data that may be displayed to a user.

In some implementations, the wearable display device 100 may comprise a glove or other article of clothing. For example, the wearable display device 100 may be part of a long sleeved shirt, sweater, or jacket. In some implementations the wearable display device 100 includes at least one display region that is capable of operating in a curved state. In some implementations the wearable display device 100 includes at least one display region that is capable of operating in wrinkled state.

As shown in the illustrated example in FIG. 1, the display area 110 is subdivided into three display regions 120, 130, and 140. The wearable display device 100 may also include one or more of the following exemplary components: memory, a processor, an audio processing unit, a speaker, a microphone, a communication system, input and output controllers, a touch screen, input devices, and the like. Each display region 120, 130, and 140 is capable of operating in a curved state.

In the illustrated implementation, the display area 110 of the surface area of the wearable display device 100 may cover only a portion of the wearable display device 100 as illustrated in FIG. 1. However, in other implementations, the display area or region 110 may extend further around the users arm and may even encompass the entire wearable display device 100, such that wearable display device 100 is configured to display images on the entire surface area of the wearable display device 100. In other words, while only one the side of the wearable display device 100 is illustrated, portions of the device 100 that are hidden from view in FIG. 1 may also be configured to display images. In one implementation, the display area 110 of the wearable display device 100 may be roughly 8 inches in length, and have a width of 6 inches at its widest point, but other shapes and sizes may also be used as appropriate.

In some implementations, the wearable display device 100 includes one or more input mechanisms, such as touch screen functionality, gesture sensing functionality, buttons, dials, or knobs. In one implementation, the wearable display device 100 includes a touch-sensitive region aligned with the display area 110, although in some other implementations the touch-sensitive regions may extend outside of the display area 110 or may cover only a portion of the display area 110.

The input mechanisms allow a user to interact with the wearable display device 100. A user may, for example, launch applications, interact with one or more applications, or rearrange applications on the display area 110 by touching the display area 110 and/or the wearable display device 100 or otherwise interacting with an input mechanism of the wearable display device 100. In some implementations, the wearable display device 100 can be configured as a "rolling" display, in which a user may scroll the displayed images around the circumference of the user's arm (e.g. up and down as shown in FIG. 1). In some implementations, the user may be able to zoom in and out within a display region, or may zoom to expand or reduce the number of display regions used to display an application or user interface element.

In some implementations, wearable display device 100 includes at least one component that is capable of bending over at least a 180 degree arc. In other implementations, the wearable display device 100 includes at least one component that is capable of bending over at least a 270 degree arc. In other implementations, the wearable display device 100 includes at least one component that is capable of bending over at least a 360 degree arc. In some implementations, the at least one component includes a display. In some implementations, the wearable display device 100 includes at least one display that can be deformed into a substantially tubular shape.

Furthermore, not every component of the wearable display device 100 is required to be curved and/or flexible. In some implementations the wearable display device 100 includes one or more substantially planar surfaces. In some implementations the wearable display device 100 includes one or more rigid components. The one or more rigid components may be curved. In some implementations, the wearable display device 100 may be semi-rigid, such that it is capable of being bent and/or flexed and remain in the bent and/or flexed state.

The wearable displays devices 100 disclosed herein may include one or more sensors that are configured to determine the orientation of the display. The sensors may include, for example, motion sensors, accelerometers, gyroscopes, light detectors, gaze detectors, thermal sensors, cameras, and the like. In some implementations, the sensors may be embedded into the device 100. In some implementations, the sensors are embedded into the display area 110.

The display area 110 may be configured such that information is displayed on sections of the display area 110 based on their visibility to a user. For example, the devices 100 described herein may be configured to determine a display area within a wearable display that is currently visible to the user and then to display content in the display area that is currently visible. In an implementation in which the display area 110 wraps more than 180 degrees around the arm of a user, the displayed image data may move to remain visible to the user as the users arm moves or twists.

It can be seen in FIG. 1 the display area 110 is displaying image data from three different applications in display regions 120, 130, and 140 of display area 110. Image data in the form of video content 101 from a first application is being displayed in display region 120, image data from a second application in the form of weather information 103 is being displayed in display region 130, and image data from a third application in the form of stock market information 105 is being displayed in display region 140. In the illustrated implementation, display region 120 may be capable of displaying image data at a higher quality than display regions 130 and 140.

The wearable display device 100 may include driver circuitry configured to display image data within the various display regions 120, 130, and 140 of display area 110, and may provide part of an interface between a processor generating image data and the display region on which the image data is displayed. In some implementations, discrete driver circuitry may be associated with each of the display regions 120, 130, or 140, or with a subgroup including multiple display regions. For example, the driver circuitry may include a first driver circuitry in electrical communication with a first display area and a second driver circuitry in electrical communication with a second display area. In other implementations, the driver circuitry may include a first driver circuitry in electrical communication with a first display sub-region of a display area and a second driver circuitry in electrical communication with a second display sub-region of the display area. In other implementations, a single display driver may be configured to display at least two different image qualities within the display area 110.

In the illustrated implementation, the display region 120 is capable of displaying data at a first image quality, and the second and third display regions 130 and 140 are capable of displaying data at a second image quality. In some implementations, differences in the capabilities of the various display regions to display image data are due to physical differences between the various display regions. For example, two or more discrete subdisplays with differing characteristics may be positioned close to one another to form display area 110, with each individual subdisplay serving as a display region or being subdivided into multiple display regions. In a particular implementation, a first subdisplay may form display region 120, and a second subdisplay may be divided into display regions 130 and 140. In other implementations, differences in driver circuitry or image data may cause the display regions to display data at different image qualities. In further implementations, display region 130 may be capable of displaying image data at a second image quality while display region 140 may be capable of displaying image data at a third image quality different than the first and second image qualities. In still further implementations, the display area 110 may include additional display regions capable of displaying image data at any of a range of image qualities.

The term image quality is used herein to refer to a variety of display characteristics, any number of which can differ between various display regions. For example, differences in image quality can include, but are not limited to, differences in pixel density, image resolution, frame rate, color depth, color gamut, sharpness, brightness, and contrast.

For example, in some implementations, the first display region 120 has a higher pixel density than the second display region 130 and the third display region 140, allowing the first display region 120 to display image data at a higher resolution than the second display region 130 and the third display region 140. For example, the first display region 120 may have about 300 pixels per inch (PPI) while the second display region 130 and the third display region 140 may have a lower pixel density, such as 100 PPI. A display area 110 which includes lower density pixel regions may decrease the overall cost of the wearable display device 100. The lower pixel density regions may also consume less power than the higher pixel density regions, as it may require less power to both generate and display the image data for the lower pixel density regions.

In other implementations the physical pixel density is substantially uniform across the display area 110, but certain display regions may be driven with a lower effective pixel density. For example, the first display region 120 may have about the same pixel density as the second display region 130 and the third display region 140. In such implementations, the driver hardware and/or software may be configured to provide a lower effective pixel density in the second display region 130 and the third display region 140. For example, multiple adjacent pixels can be driven together as a single pixel, lowering the effective resolution of the display, or alternating pixels or lines may be left undriven. In such an implementation, the display area 110 may be divided into two or more display regions in a dynamic manner, in which the display regions need not be located in a fixed position within the display area 110. Rather, the display regions may be moved around within the display area 110 and re-sized and/or reshaped as desired.

In some implementations, the first display region 120 is capable of displaying image data having a first color depth and the second and third display regions 130 and 140 are capable of displaying image data having a second and/or third color depth. Color depth, also referred to as bit depth, may refer to the number of bits used to indicate the color of a single pixel or the number of bits used for each color component of a single pixel. For example, in some implementations the first color depth may be 16-bit color and the second color depth may be 8-bit color. In some implementations, at least a portion of the display area 110 may be configured to display 1-bit or 2-bit color. For example, simple text may be displayed in 1-bit or 2-bit color to conserve energy and promote battery life. Thus, the wearable display device 100 may include various sub regions capable of displaying image data at a variety of color depths.

In some implementations, the first display region 120 is capable of displaying image data at a first frame rate and the second and third display regions 130 and 140 are capable of displaying image data at a second and/or third frame rate. For example, in some implementations the first frame rate may be 30 frames per second and the second frame rate may be 15 frames per second. Thus, the wearable display device 100 may include various display regions that are capable of displaying content at a variety of different frame rates. In some implementations, the differences in frame rate may be due to physical differences between the display regions, or the capabilities of the associated driver circuitry or other device components. In such implementations, the display regions may be fixed, such that a first display region is only capable of displaying image data at a first maximum frame rate, and a second display region is only capable of displaying image data at a second maximum frame rate. In other implementations, the frame rate may be a function of the image data provided to the display area 110 and may be variable and/or dynamic across the display regions.

In some implementations, the first display region 120 is capable of displaying image data having a first color gamut and the second and third display regions 130 and 140 are capable of displaying image data at a second and/or third color gamut which may be different than the first color gamut. In general, color gamut refers to the complete subset of colors that the driver circuitry is configured to display. In some implementations, for example, a first sub-region may be capable of displaying a first color gamut that is broader than a second color gamut associated with second sub-region of the wearable display device 100. In some implementations, certain display regions of the display area 110 may only be capable of displaying a given color gamut, which may be due to physical characteristics of the display region or may be due to the associated driver circuitry or other device components.

In some implementations, the first display region 120 is capable of displaying image data having a first brightness level and the second and third display regions 130 and 140 are capable of displaying image data at a second and/or third brightness level which may be different than the first brightness level. In some implementations, the certain display regions of the display area 110 may only be capable of displaying images at a given brightness level. The range of brightness which can be displayed by a portion of a device may be constrained by physical characteristics of a display region, or by the associated driver circuitry or other device components.

Even in some implementations in which physical differences in the display regions or associated driver circuitry limit the image quality of some display regions relative to other display regions, a display region capable of displaying image data at a high image quality may nevertheless be driven at a lower image quality if desired. In some implementations, the wearable display device 100 can dynamically adjust the image quality. Such an adjustment may be made in response to one or more of user input, application output, and content of the image data to be displayed. For example, when relatively static text is displayed in the first display region 120, the content may be displayed at a relatively low frame rate. However, when video is displayed in the same display region 120, the frame rate may be increased to a relatively higher frame rate.

In some implementations, one aspect of image quality may be higher in a first display region while a different aspect of image quality may be higher in a second display region. For example, a first display region 120 may be capable of displaying image data at a frame rate higher than that of a second display region 130, while the second display region 130 may be capable of displaying image data at a resolution higher than that of the first display region 120. Such a configuration may allow various display regions to be optimized to display specific types of data.

Figure 2A:
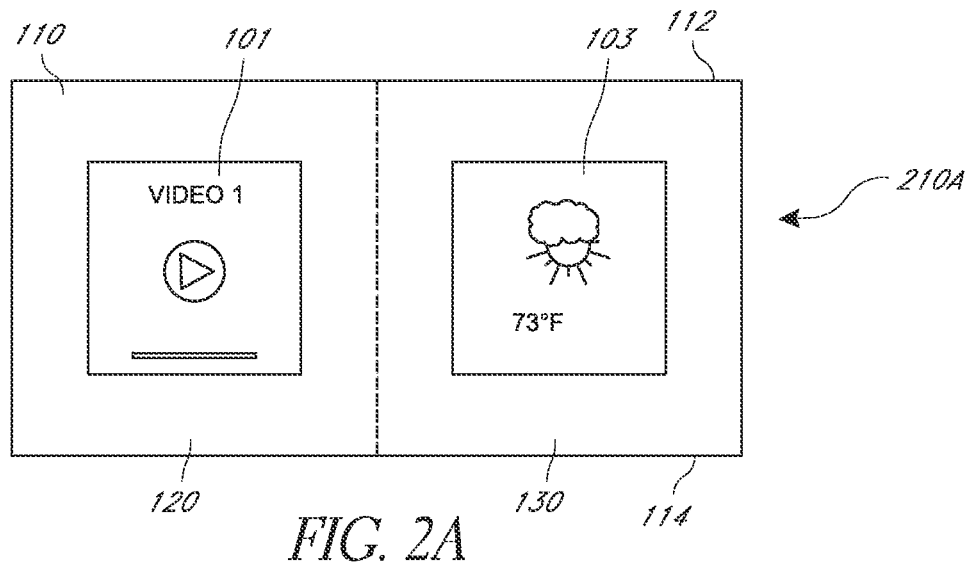
FIGS. 2A-2D depict various example implementations of displays including a plurality of display regions.

Various sizes and shapes of displays and display regions can be used. FIGS. 2A-2D depict various implementations of displays including a plurality of display regions. FIG. 2A illustrates a rectangular display 210A which is subdivided into a first display region 120 and a second display region 130, with the facing edges of the first and second display regions 120 and 130 abutting one another. The first display region 120 is displaying video content 101 while the second display region 130 is displaying weather information 103.

Due to the rectangular shape of the display 210A, the upper edge 112 and lower edge 114 of the display area 110 are two substantially parallel lines formed by the upper and lower edges of the display regions 120 and 130. Although the two display regions 120 and 130 are referred to as abutting one another, there may be some spacing between the two display regions 120 and 130 for additional components, particularly in implementations in which two different displays are combined to form display area 110.

Figure 2B:
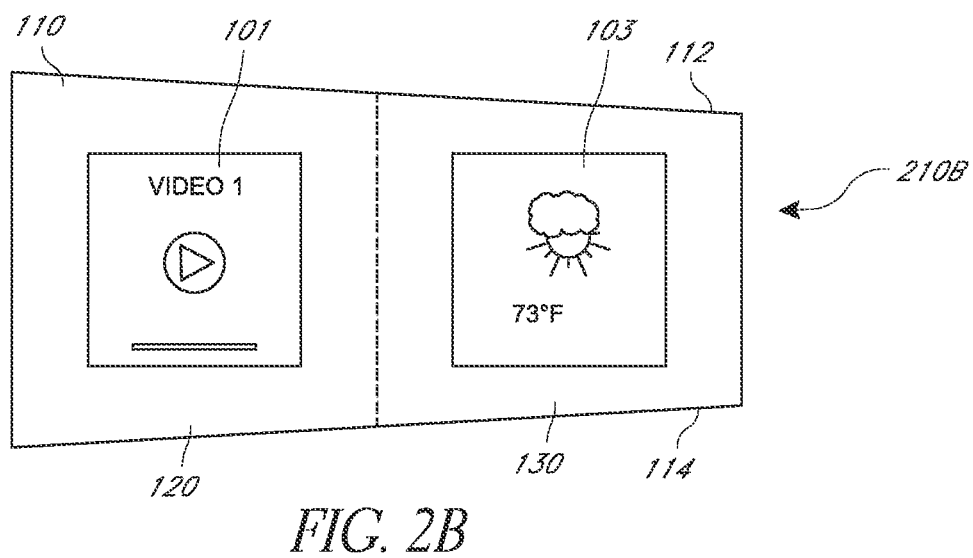

FIG. 2B illustrates another implementation of a display 210B which is subdivided into a first display region 120 and a second display region 130. The display 210B differs from the display 210A of FIG. 2A in that the display 210B is generally in the shape of a parallelogram instead of a rectangle, with the upper and lower edges 112 and 114 of the display 210B oriented at an angle to one another. A tapering display such as display 210B may be well-suited for use as a component of a wearable display, due to the narrowing shape of a user's forearm. In some implementations, one or more display regions taper in size from the elbow to the wrist of a user.

Figure 2C:
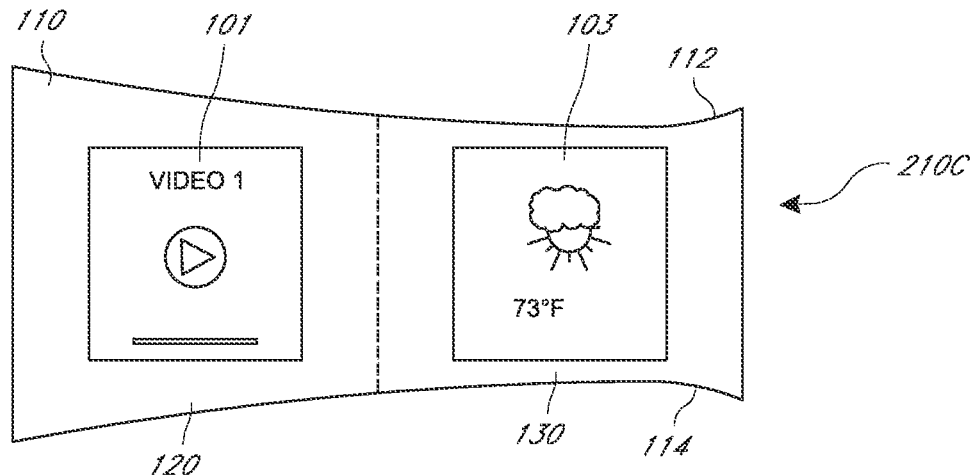

FIG. 2C illustrates another implementation of a display 210C which is subdivided into a first display region 120 and a second display region 130. Like display 210B of FIG. 2B, the display 210C of FIG. 2C is also a tapering shape, but differs in that the upper and lower edges 112 and 114 are concave lines, rather than straight lines. In other implementations, other non-straight edges may be used, such as convex lines, or lines with an angle or other discontinuity.

Figure 2D:
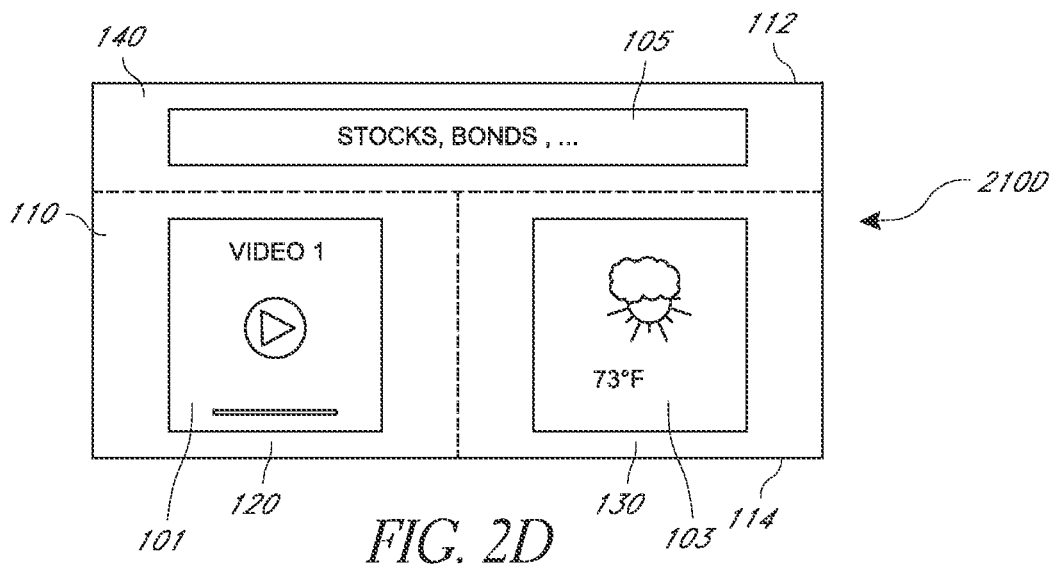

FIG. 2D illustrates a rectangular display 210D which is subdivided into a first display region 120, a second display region 130, and a third display region 140. Unlike the display regions of FIG. 1, the third display region 140 in the display 210D of FIG. 2D is extends horizontally across the entire length of the display 210D. In the particular implementation illustrated in FIG. 2D, the third display region 140 is thin compared to the other display regions 120 and 130, but in other implementations can be made thicker or thinner than the implementation illustrated in FIG. 2D.

In other implementations, additional display regions may also be used. In other implementations, the boundaries between display regions need not be generally horizontal or vertical straight lines as depicted in certain illustrations herein, but may be in any appropriate orientation or shape.

Figure 3A:
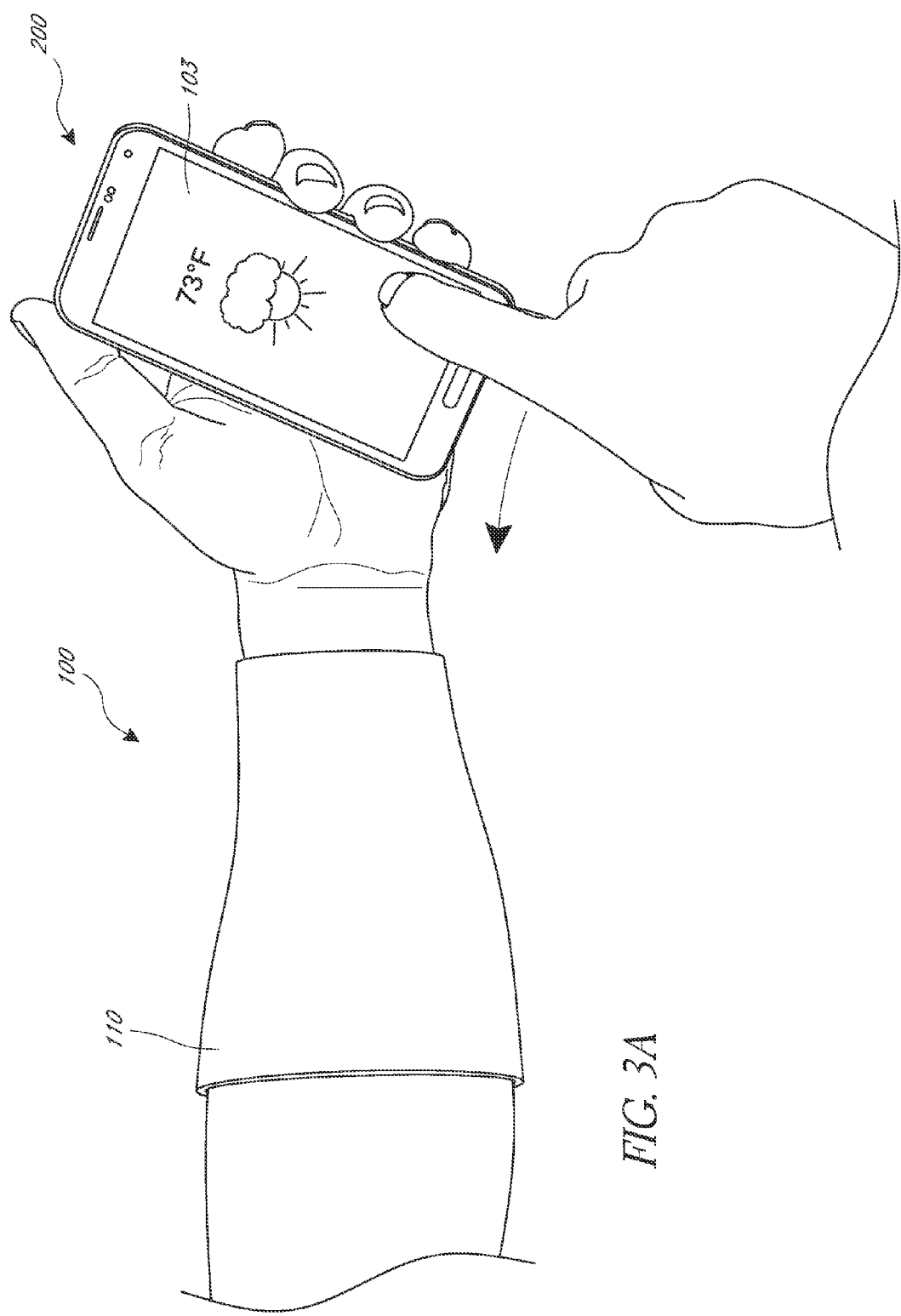
FIGS. 3A and 3B illustrate an implementation in which a mobile phone serves as a complementary device for a wearable display device.
Figure 3B:
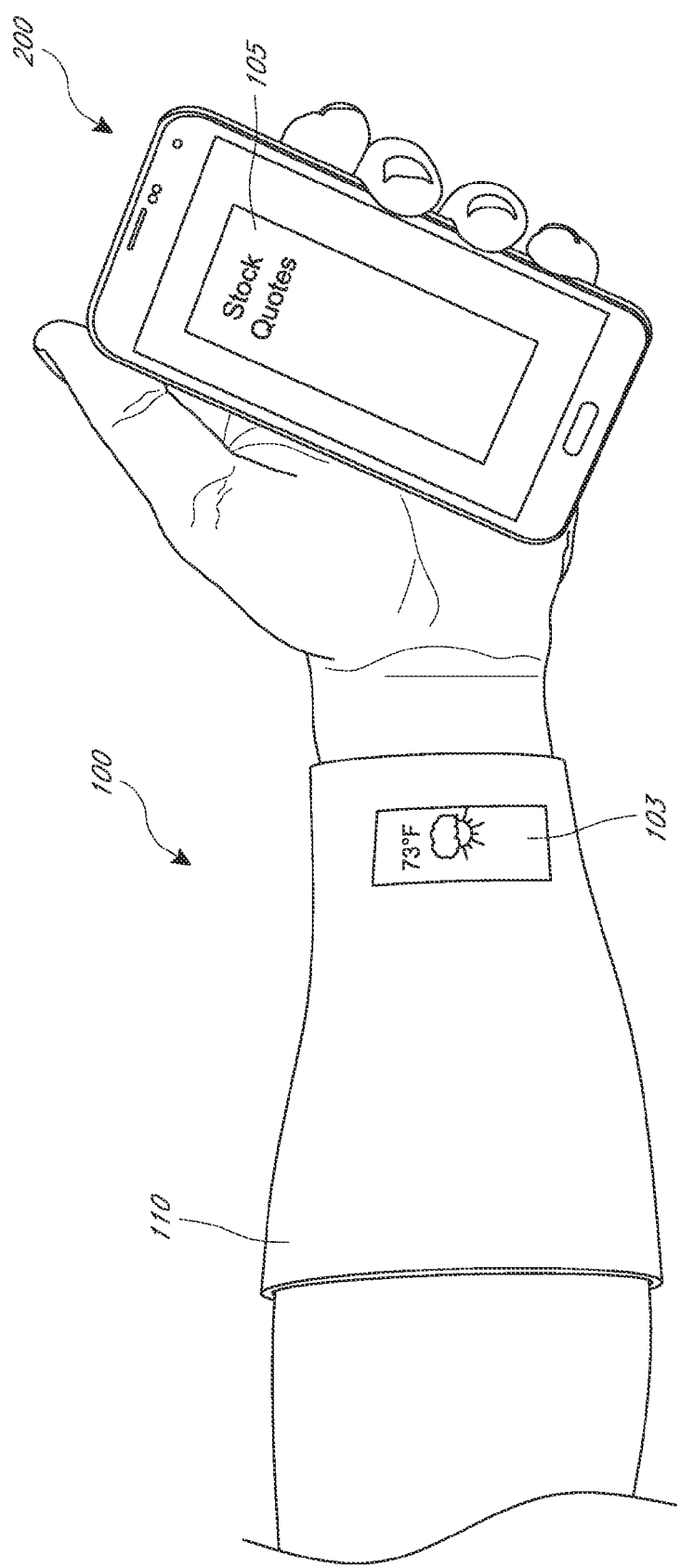

FIGS. 3A and 3B illustrate an implementation in which a mobile phone serves as a complementary device 200 for a wearable display device 100. The wearable display device 100 may be configured to be physically or wirelessly coupled to a complementary device 200 such as a smartphone. The complementary device 200 can be any suitable device such as a computer, laptop, smartphone, smart-television. In this way, the control of the display of the images in the display area 110 of the wearable display device 100 may be at least partially controlled by the complementary device 200. In some implementations, the wearable display device 100 may mirror the display of the complementary device 200. In other implementations, the wearable display device 100 displays at least a portion of the image data being displayed by the complementary device 200. In some implementations, the wearable display device 100 may be dependent upon the complementary device 200 and may be connected either directly or wirelessly to the complementary device 200. In other implementations, the wearable display device 100 may be fully functional without the complementary device 200 but can also be used in a mode in which the complementary device 200 interacts with the wearable display device 100.

In some implementations, the wearable display device 100 may be capable of interacting with and/or at least partially controlling the complementary device 200. For example, in some implementations, the wearable display device 100 may be configured such that a user can select a display region and/or application displayed on the wearable display device 100 and choose to have that display region and/or application displayed on a complementary device 200.

In the implementation illustrated in FIGS. 3A and 3B, an application or other user interface element may be selected on the complementary device 200 and moved onto the display area 110 of the wearable display device 100, such as by swiping across the display of the complementary device 200. The complementary device 200 may be capable of running one or more applications or programs capable of displaying image data on the wearable display device 100 or otherwise communicating with an application or program on the wearable display device 100 to display image data on the wearable display device 100. In some implementations, the wearable display device 100 is running one or more applications or programs capable of displaying image data on the wearable display device 100. That is to say, the display area 110 of the wearable display device 100 is capable of displaying image data that is output and/or rendered by an application or program running either on the wearable display device 100 or on an associated complementary device 200.

Figure 4A:
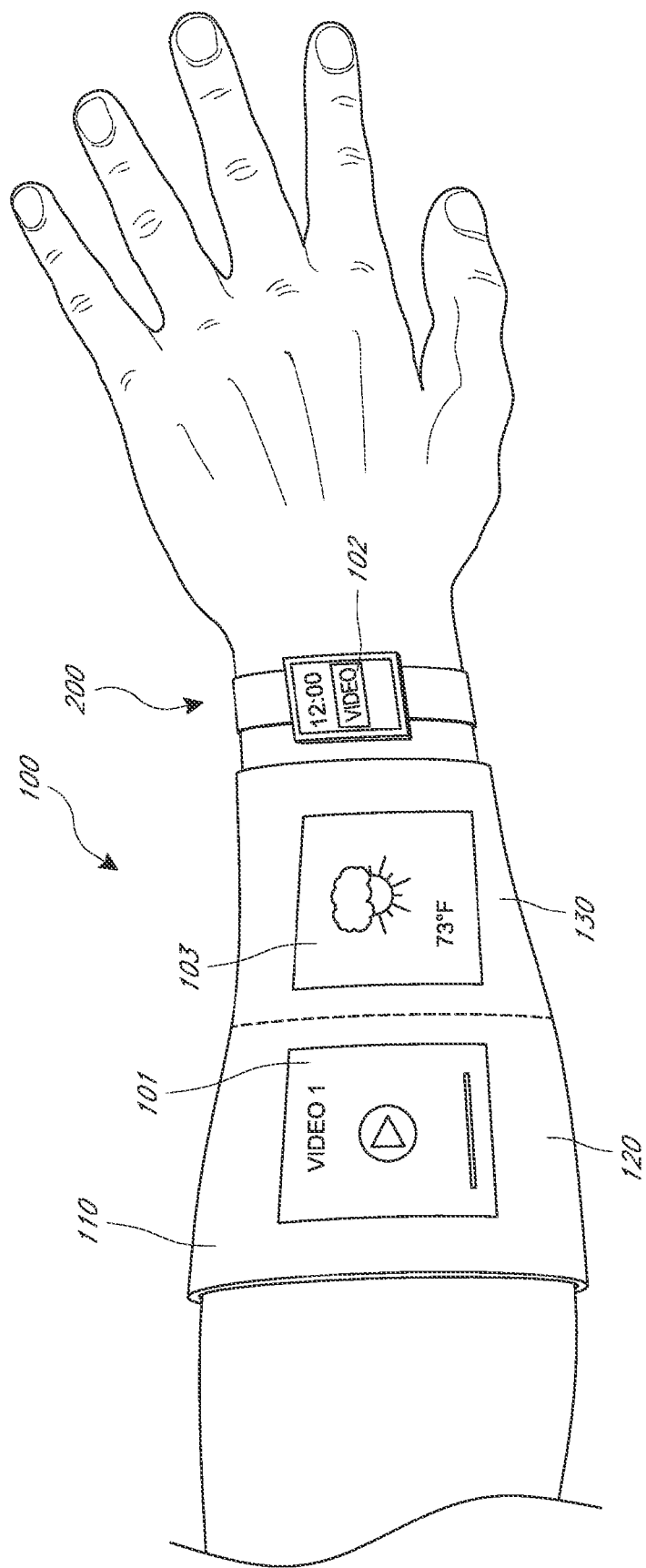
FIGS. 4A and 4B illustrate an implementation in which a smart watch serves as a complementary device for a wearable display device.
Figure 4B:
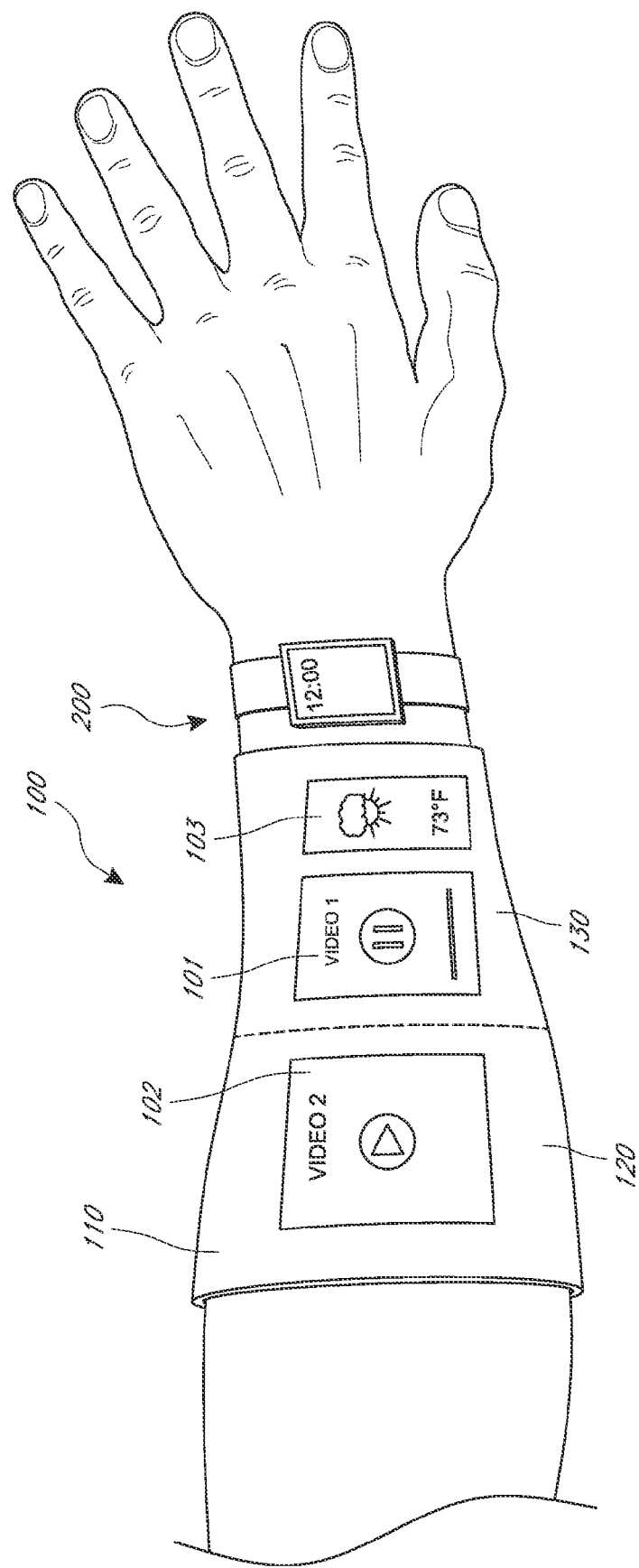

FIGS. 4A and 4B illustrate an implementation in which a smart watch serves as a complementary device 200 for a wearable display device 100. In some implementations, the watch may be a complementary device 200 which houses components that are not flexible enough to be included in the wearable display device 100. In some implementations, the watch may house components which are heavier and/or less-breathable than other components of the wearable display device 100.

FIGS. 4A and 4B also illustrate that the display 110 may include a first display region 120 and a second display region 130. As discussed above, the first display region 120 may be capable of or configured to display images within the first display region 120 at a first image quality, while the second display region 130 may be capable of or configured to display images within the second display region 130 at a second image quality. The second image quality may be different from the first image quality. In the particular implementation illustrated in FIGS. 3A and 3B, the second display region 130 is configured to display images at an image quality is less than the image quality the can be displayed in the first display region 120. However, in some implementations the second display region 130 may be configured to display higher-quality images than the first display region 120.

While the illustrated implementation of FIGS. 4A and 4B illustrates the display regions 120 and 130 as regions that are divided in a direction extending roughly perpendicular to an axis extending roughly parallel to a user's forearm, the display regions may be divided up in any manner. If the display 110 wraps around the user's forearm, the display regions may be similar in shape to bands or rings circling a part of the user's forearm. In other implementations, the display is divided into a plurality of elongated display regions that run roughly parallel to the user's forearm.

It can be seen in FIGS. 4A and 4B that display regions 120 and 130 each include an upper boundary running roughly parallel to the user's forearm on the top side (e.g. the side closer to a user's thumb), which together form the upper edge of the display 110. The display regions 120 and 130 may also include a lower boundary running roughly parallel to the user's forearm on the bottom side (e.g. the side closer to a user's pinky), which together form the lower edge of the display 110. The display regions 120 and 130 share a boundary line extending roughly perpendicular between the upper and lower boundary that roughly divides the display 110 generally in half to define the two display regions 120 and 130. In some implementations, the boundary lines defining the sub-regions are dynamic. In other words, the sub-regions may be re-sized and/or re-configured. In other implementations, the boundary lines are static and unchanging, and may be the boundaries between two discrete displays combined to form display 110.

As shown in FIG. 4A, the first display region 120 may display video content 101 and the second display region 130 may display weather content 103. Because the weather content 103 is generally static and primarily text-based while the video content 101 is more dynamic in comparison to the weather content 103, the video content 101 may be displayed in a first display region 120 that is capable of or configured to display content at a different image quality than the second display 130 region. In some implementations, the first display region 120 may be capable of or configured to display content at a higher resolution, frame rate, color depth, color range, and/or color gamut than the second display region 130. In this way, the video content 101 may be displayed in a different manner from the weather content 103. Thus, in some implementations, content that will benefit from being displayed at a higher image quality (e.g. video content) may be displayed in the first display region 120 and other content may be displayed on the second display region 130.

As shown in FIGS. 4A and 4B, the wearable display device 100 may interact with a complementary device 200. As shown in FIG. 4A, a first video content 101 is being displayed in the first display region 120, weather content 103 is being displayed in the second display region 130, and a second video content 102 is being displayed on the display of the complementary device 200. In some implementations, the user may wish to view the second video content 102 in a larger format. As such, in some implementations, the user may cause the second video content 102 to be displayed on the wearable display device 100 by interacting with the mobile device 200. In turn, the wearable display device 100 and/or the mobile device 200 may cause the second video content 102 to be displayed in the first display region 120 as shown in FIG. 4B. The second display region 130 may be dynamically divided into a second display region 130 and a third display region 140, as shown. The first video content 101 may be paused and/or displayed in second display region 130, and the weather content 103 moved into the third display region 140 when the second video content 102 is selected for viewing in the first display region 120. The second display region 130 may be dynamically divided into a second display region 130 and a third display region 140, as shown.

In some implementations, one or both the wearable display device 100 and/or the complementary device 200 may be configured to select a region of the display 110 in which to display particular image data. One or both of the wearable display device 100 and/or the complementary device 200 may include a processor configured to select a region of the display 110 to display the selected image data. In some implementations, the processor is configured to select a region within the display 110 to display data based at least in part on the content of the data to be displayed. That is to say, the processor may be configured to determine the type of image data or content that an application will display. For example, the processor may be configured to determine if the application will display static text, scrolling text, photos, animations, and/or videos. In some implementations the processor determines the type of content at least in part by the file type extension of the content to be displayed. The processor can then determine which region within the display 110 is best suited to display the content.

In some implementations, the processor is configured to select a region within the flexible display area 110 to display data based at least in part on the type of software application that wishes to display content. In some implementations, the processor is configured to select a region within the flexible display area 110 to display data based at least in part on the rate and/or amount of data being received from the application. For example, multiple commands to refresh the display may be indicative of animation and/or video. In response, the processor may be configured to direct the display data to the optimal sub-region of the display for displaying animation and/or video.

Other aspects of the display data may be used to at least partially determine the optimal sub-region for displaying various types of content on the wearable display. For example, in some implementations, the processor is capable of determining, for example, the number of colors or range of colors to be displayed, the frame rate, the level of detail in the frequency domain, the size, shape, and/or area of the content window, and/or the brightness level of the content to be displayed. The processor can then determine which region within the display 110 is best suited to display the content.

In some implementations, the processor may compare one or more aspects of the display data from one or more applications and determine the optimal sub-regions for displaying the data. The processor may compare, for example, the number of colors in the image data from a first application to the number of colors in image data from a second application and direct the image data from the application generating image data which includes more colors to a to sub-region of the display that is capable of displaying more colors. In another example, the processor may compare the relative sizes and/or shapes of the content windows from applications and determine the sub-region that is best utilized for the size and/or shape of the content. For example, a content window that is relatively narrow and elongated may best be displayed on a sub-region of the display that has a corresponding shape and/or in a sub-region that has a relatively greater curvature while a content window that is substantially square may best be displayed in a sub-region that has a corresponding shape and/or in a sub-region that has a less curvature. In another example, the processor may perform a fast Fourier transform ("FFT") algorithm on two or more sets of image data to determine the relative sharpness of the images to be displayed and direct the sharper images to a display region that is capable of displaying higher resolution images. In another example, the processor may compare the refresh rates and/or the level of complexity in the image data in order to determine which content would most benefit from a display region having better display capabilities.

In some implementations, the relative battery life of the wearable display and/or companion device may be used to at least partially determine where and/or how various types of content are displayed on the display 110. For example, if the battery life is determined to be below a threshold value, the processor may direct display data to sub-regions of the display 110 that consume less power. In some implementations, the threshold value may be selected by the user. In some implementations, the driver circuitry may be configured to drive the display 110 at a lower image quality when the batter is low, such as by decreasing brightness levels, decreasing the number of colors displayed, and/or decreasing the frame rate. In some implementations, displayed content may be moved from sub-regions that consume more power to sub-regions that consume less power in order to prolong the use of the wearable display.

While the processor may be capable of determining a preferable or optimal sub-region of the display to display various types of content without user input, selection of a display region can in some implementations also be made by a user selecting a display region where content is displayed. For example, with reference to FIG. 4B, a user may wish to view the weather content 103 in the first display region 120 even if the processor determines that the weather content 103 is best displayed in the second display region 130. In some implementations, when a user opens an application, a pop-up window may prompt the user to select where to display the application content. In some implementations, a pop-up window recommends where to display the application content and the user can either agree or disagree and select where to display the content. In other implementations, user input such as touch or gesture input can be used to move content to other regions of the display.

Figure 5:
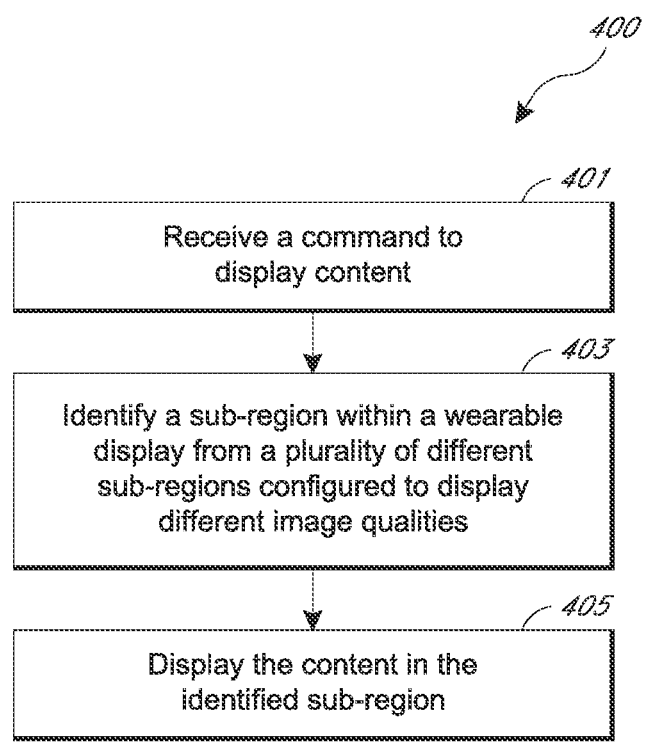
FIG. 5 is a flow diagram illustrating an example method for operating a wearable display device.

FIG. 5 is a flow diagram illustrating an example method 400 for operating a wearable display device 100 is shown. While the steps in the flow diagrams depicted in the present disclosure are illustrated in a particular order, the various steps are only arranged in these orders as examples and are not limited to the specific order or hierarchy presented. In addition, all of the steps may not be necessary. Moreover, the methods disclosed herein use may include additional steps that are not explicitly illustrated by flow diagrams. As shown in FIG. 5, the method 400 may begin at block 401 by receiving a command to display content. The command may be received from a user interface, or may be triggered without immediate user interaction, such as when an email is received or an alarm goes off. In some implementations, the command is received from one or more software applications.

The method 400 may continue at block 403 by identifying a display region within a wearable display suitable for displaying the content. The wearable display may include a plurality of different display regions, with different display regions capable of or configured to display different image qualities. The image quality may include one or more display characteristics such as resolution, frame rate, color gamut, and color depth. The identification of the appropriate display region may be based at least in part on the software application that desires to display the content.

In some implementations software applications may have an associated image quality priority ranking. In such implementations the identification of the appropriate display region may be based at least in part on the priority ranking of the application relative to other applications simultaneously displaying image data. In some implementations, the priority ranking may be user selected or based at least in part on user preferences. User preferences may be part of a user profile that may be stored on the wearable display device 100 or a companion device. In this way, more than one user may customize the wearable display device 100 and/or the display area 110. For example, a first user may prefer to have particular content displayed in the same sub-region of the display at all times, while second user may have different preferences. In some implementations, the wearable display device 100 may be configured to utilize one or more biometric parameters to identify which of a plurality of users is currently wearing the wearable display device 100 and select one of a plurality of user profiles. For example, the wearable display device 100 may be configured to select a particular user profile based at least in part on how much the wearable display device 100 is stretched when worn by the user. In another example, the wearable display device 100 may be configured to select a particular user profile based at least in part on another biometric parameter, such as average heart rate, temperature, and/or blood pressure. In another example, the wearable display device 100 may use one or more sensors to determine the relative size of the arm that the wearable display device 100 is wrapped around in order to determine which user is wearing the device 100. For example, one or more strain gauges or pressure sensors could be used to determine the relative approximate diameters of one or more sections of the wearable display device 100 when a user is wearing the device 100 in order to identify the wearer and select a user profile associated with the user.

In some implementations the priority ranking may change dynamically. For example an application that receives a notification or desires to display a notification to a user may be given higher priority when the application receives the notification or desires to display that notification. In some implementations, higher priority data may be displayed in a specific location, such as in display regions that are closer to a user's wrist. In this way, higher priority data can be seen more easily by a user than lower priority data.

In some implementations, a priority ranking may be determined at least in part by the processor. The processor may consider, for example, the usage history of an application and/or the usage history associated with a specific user of the wearable display device 100. Usage history may include, for example, how many times a user launches an application, how many times a user interacts with an application, how often the application refreshes and/or receives an alert, the amount of time a user displays content from a particular applications, as well as the size and/or display characteristics of the of the content to be displayed. In this way, the processor can determine the relative priority level of the applications and arrange the higher priority applications accordingly. Alternatively and/or in addition, the processor may be configured to determine where to display content based at least in part on the privacy level of the content as explained in further detail below.

As a non-limiting example, first image content may be output from a first application and second image content may be output from a second application. The wearable display device 100 may include two display regions. The first display region may be positioned along a relatively planar surface extending across the top side of a user's forearm while the second display region may be positioned below the first display region on a relatively curved surface extending across the side of the user's forearm. A processor may need to choose how to best display the two image contents. In other words, the processor may compare the first image content with the second image content in order to determine which sub-region to display the content in. The processor may make the selection based in part on one or more factors. For example, the processor may consider which of the two applications are used most frequently, which of the two applications have the most running time to date, which application best fits the physical sizes of the first and second display regions, as well as one or more image qualities that are to be displayed. The first display region may be preferred for applications that are used more frequently and/or display content at a higher frequency because the first display region may be more easily seen by a user and is more easily accessible.

In some implementations the identification of the appropriate sub-region may be based at least in part on the desired image quality for the content to be displayed. For example, in some implementations the identification of the appropriate sub-region may be based at least in part on the number of different colors that need to be displayed. In some implementations the identification of the appropriate sub-region may be based at least in part frame rate of image data being output by an application.

The method 400 may move to a block 405 by displaying the content in the selected display region of the wearable display device 100. In some implementations, displaying the content in the identified display region includes moving other content currently being displayed from one display region to another display region.

In some implementations a user may actively select the display region within the display 110 in which the content is to be displayed. In other implementations, the wearable display device 100 and/or mobile complementary device 200 may automatically select the sub-region in which the content is to be displayed. In some implementations the wearable display device 100 and/or the complementary device 200 may dynamically determine which display regions will display various image data. As such, the wearable display device 100 and/or the complementary device 200 may be configured to actively move content from one display region to another, either automatically or in response to user input.

Figure 6A:
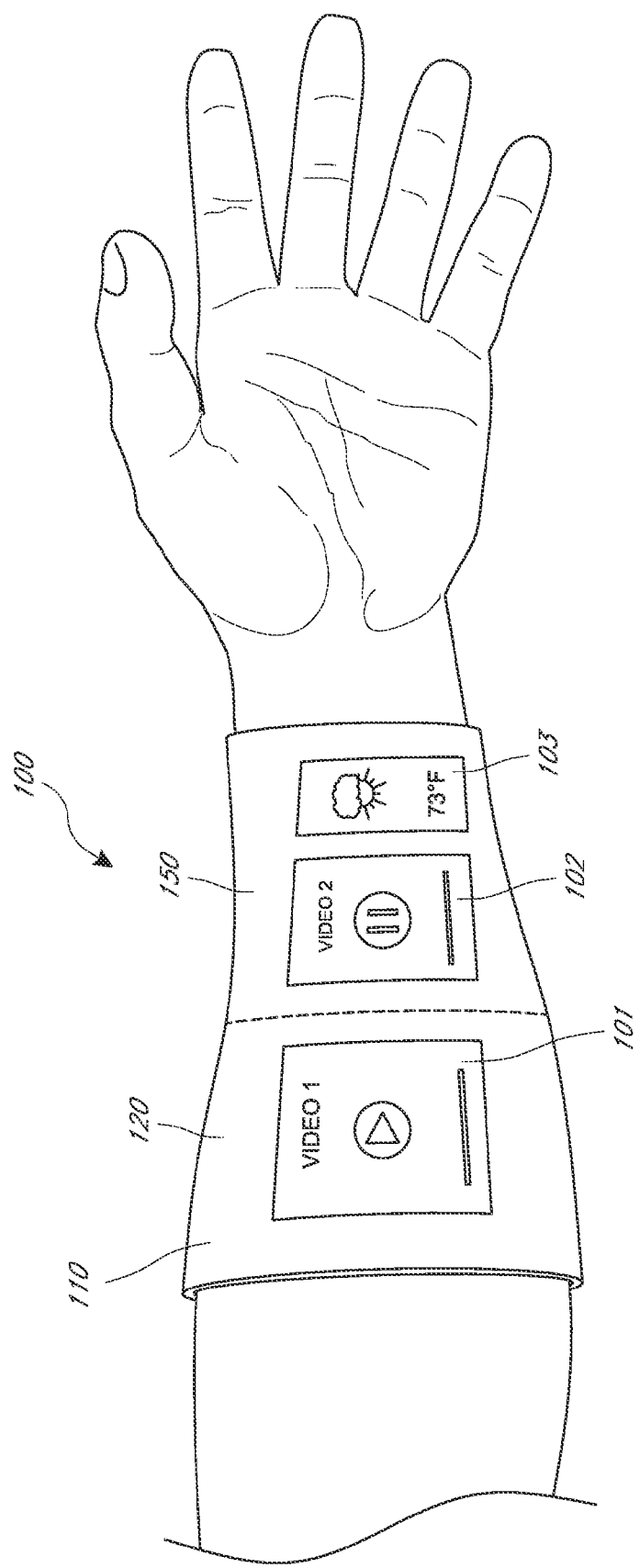
FIGS. 6A and 6B illustrate an example of content reorganization on a wearable display device.
Figure 6B:
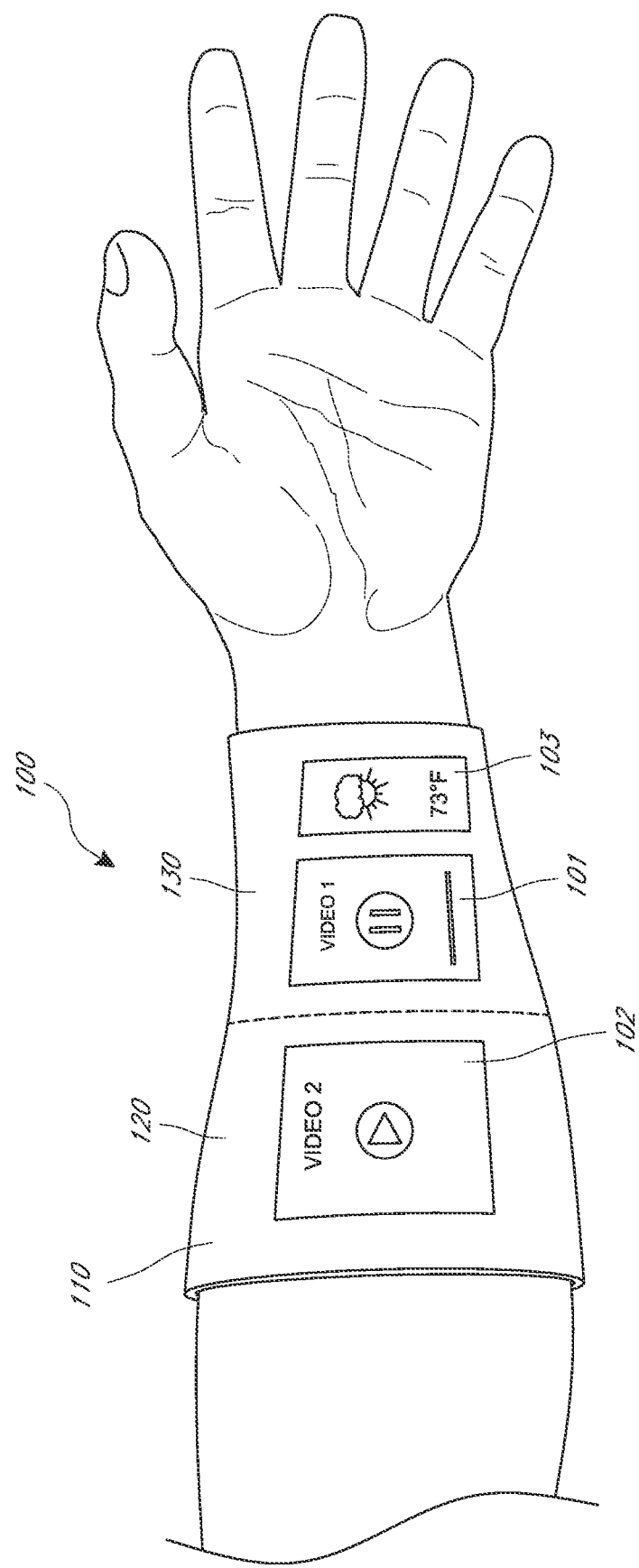

FIGS. 6A and 6B illustrate an example of content reorganization on a wearable display device 100. The wearable display device 100 may be configured to operate as a stand-alone device or may be configured to operate in conjunction with another device such as a computer, laptop, smartphone, smart-television, and the like. As shown in FIG. 6A, first video content 101 is playing in first display region 120. Second video content 102 is paused and displayed in a second display region 130, while weather content 103 is displayed in a third display region 140. In such an implementation a user may wish to resume watching the second video content 102. Thus the user may select the second video content 102, such as by contacting the area of the second display region 130 where the second video content 102 is displayed. The selection of the second video content 102 may cause the wearable display device 100 to move the second video content 102 from the second display region 130 to the first display region 120 and to move the first video content 101 from the first display region 120 to the second display region 130 as shown in FIG. 6B. The first video content 101 may be paused when moved to the second display region 130.

Figure 7A:
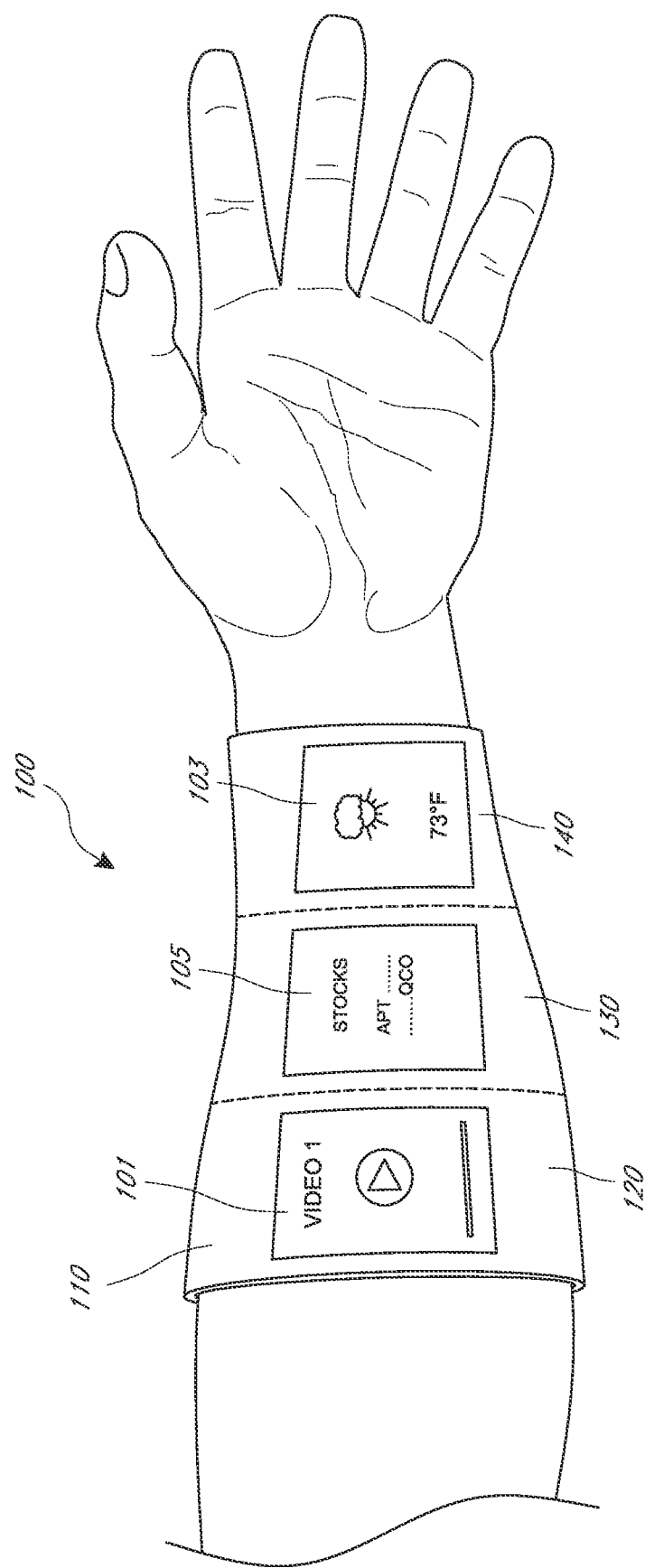
FIGS. 7A and 7B show another example of content reorganization on a wearable display.
Figure 7B:
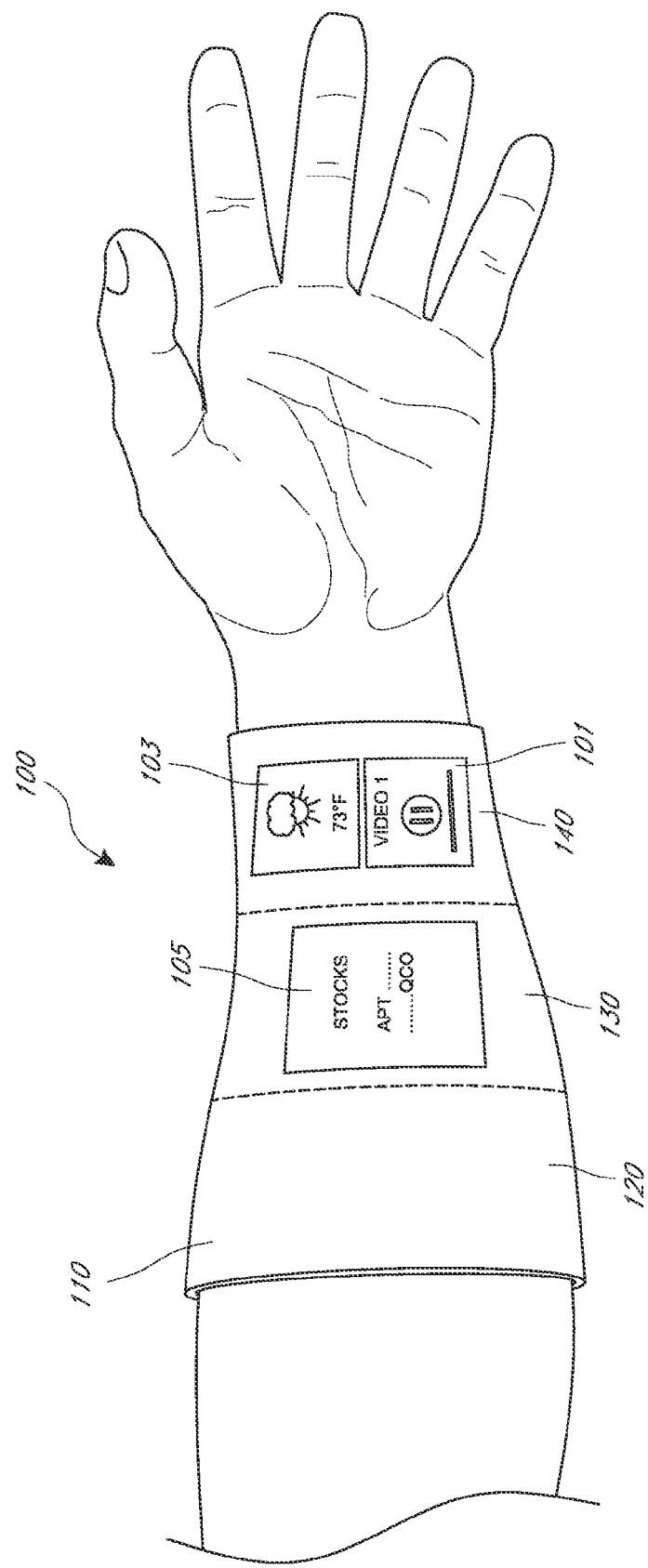

FIGS. 7A and 7B show another example of content reorganization on a wearable display. The wearable display device 100 of FIGS. 7A and 7B include the three different display regions 120, 130, and 140, each illustrated for the purpose of convenience as having approximately the same width. In the illustrated implementation, the display regions may have display capabilities that decrease with respect to at least one display characteristic from left to right, so that the first display region 120 is capable of displaying image data at a higher quality than the second display region 130, which in turn is capable of displaying image data at a higher quality than the third display region 140. However, the image quality levels may be arranged in another order or configuration in other implementations.

As shown in FIG. 7A, video content 101 is being displayed in the first display region 120, scrolling stock content 105 is being displayed in the second display region 130, and weather content 103 is being displayed in the third display region 140. This arrangement may be due to a determination made by the wearable display device 100 has that the video content 101 is best suited for display in the display region with the greatest display capability, or may be due to previous user input. Similarly, the wearable display device 100 may have determined that the scrolling stock content 105 is best suited for display in the display region with the second greatest display capability, and may have determined that the weather content 103 is best suited for display in the display region with the lowest display capability. In this way, the display of three different types of content may be optimized.

If the video content 101 is paused, as is shown in FIG. 7B, the wearable display device 100 may reassign or move the display of the video content 101 to the third display region 140. When paused, the display of the video content 101 may no longer need to be refreshed and/or displayed at a high resolution. As such, it can be moved to the display region with the lowest display capability when paused. The first display region 120 may then be powered off to reduce power consumption and extend battery life.

Figure 8A:
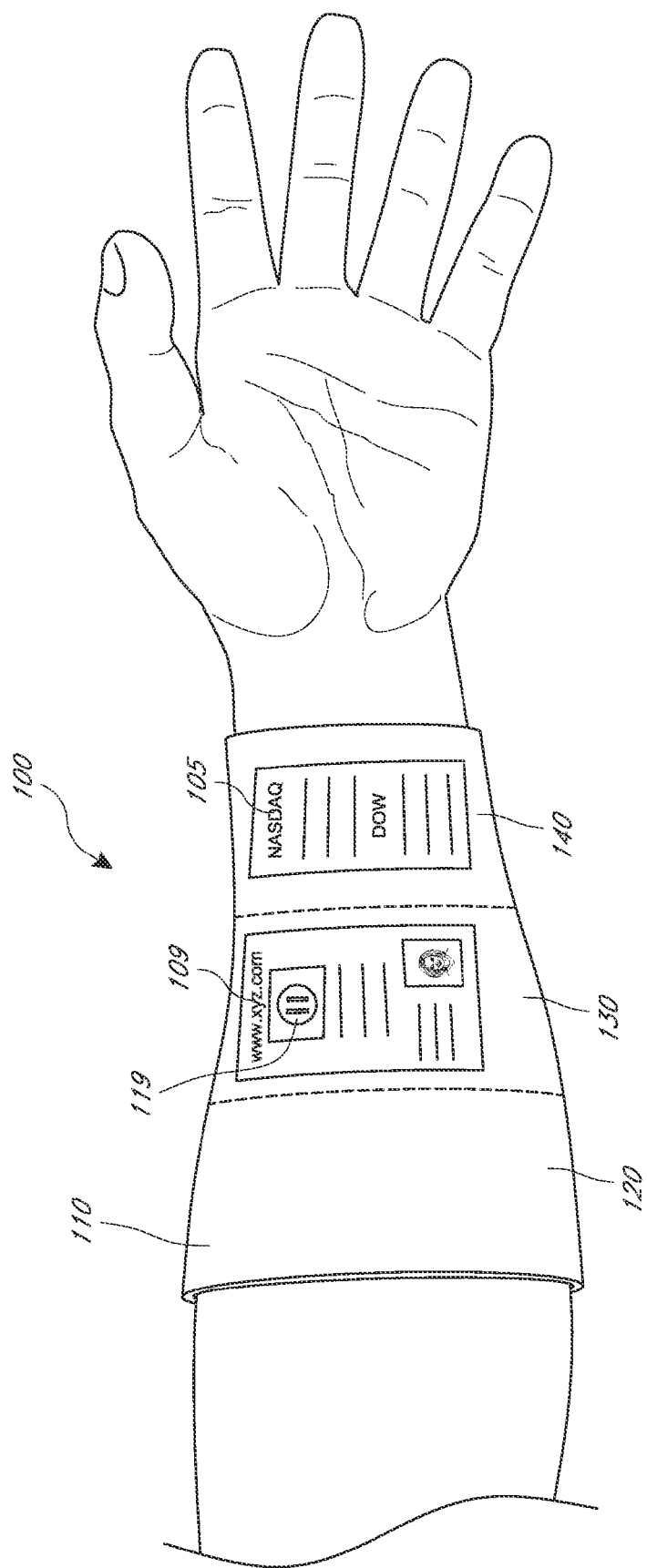
FIGS. 8A and 8B show another example of content reorganization on a wearable display.
Figure 8B:
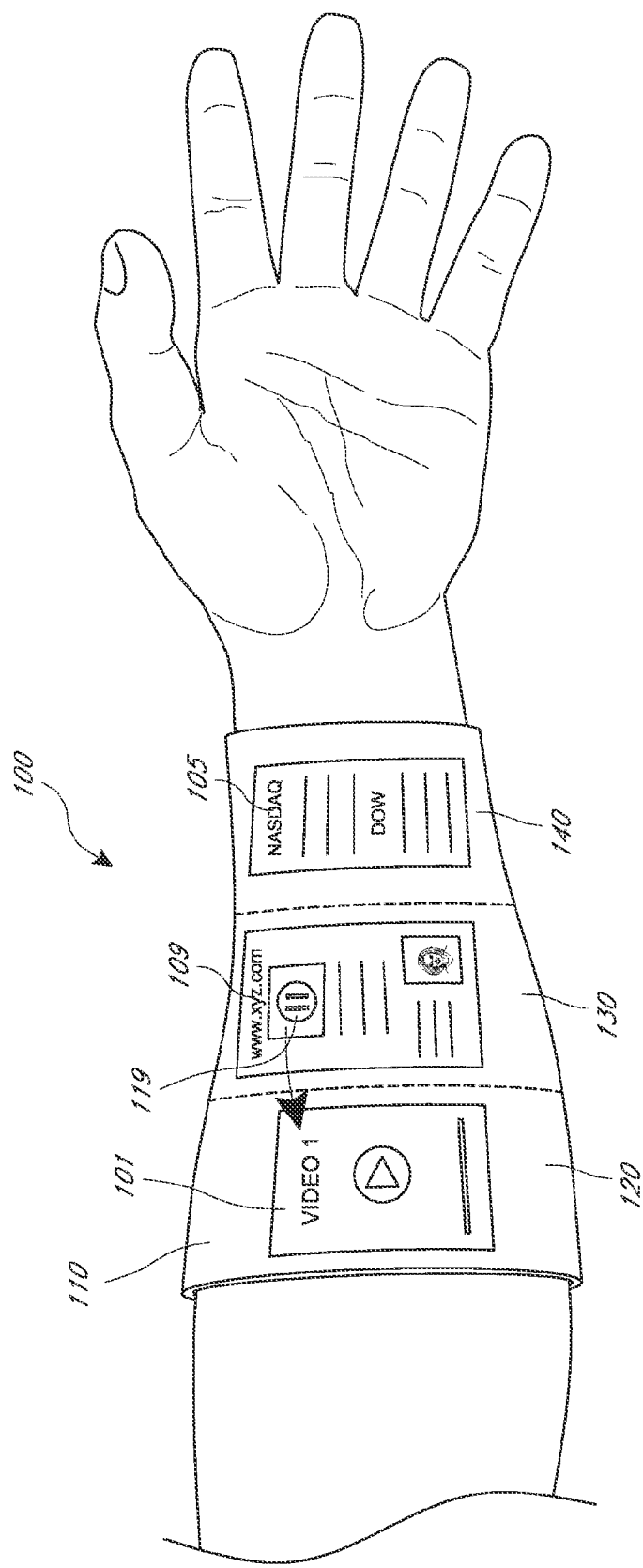

FIGS. 8A and 8B show another example of content reorganization on a wearable display device 100. The wearable display device 100 is again shown having three display regions with varying display capabilities. As shown in FIG. 8A, a web browser 109 is being displayed in the second display region 130 and scrolling stock content 105 is being displayed in the third display region. The web browser 109 may include a link to an embedded video 119. A user may wish to watch the embedded video 119. As such, when the user selects the embedded video 119, the wearable display 500 may open the video application such that the video content 101 is displayed in the first display region 120 as shown in FIG. 8B.

FIGS. 9A-12D show illustrative implementations of displaying content on a wearable display device 100 based at least in part on the relative privacy level of the content to be displayed. These implementations may be used alternatively and/or in addition to the implementations described above. As will be described in further detail below, the wearable display device 100 may include a public display region and a private display region. Certain displayed content may be constrained to a display region designated as a private display region based at least in part on a privacy level associated with the display content. The privacy levels may be dynamic and based on the type of content being displayed and/or the application from which the content arrives from. The private and/or public regions may be dynamic depending on the location, position, and orientation of the display and/or the user. The wearable display device 100 may include one or more sensors to determine the position and/or orientation of the display and/or user. In some implementations, multiple levels of privacy may be used.

In some implementations, the wearable display device 100 includes a first region having a first privacy level or threshold and a second region having second privacy level or threshold. The first and second privacy levels or thresholds may be different. Restrictions or allowances may be placed on displayed content based on privacy thresholds. In other words, in some implementations, applications can include restrictions which prevent the application from being launched or displayed in specific regions of the wearable display based on the privacy level of the information that the application intends to display. For example, emails, SMS, Facebook, and other private information may be displayed in a private region while less sensitive information such as news, stock prices, twitter feeds, and sports scores may displayed in a public or less-private region.

In some implementations, the designation of sub-regions of the display as public or private may be dynamic, and the relative sizes and locations of the public and private sub-regions can be adjusted based on, for example, how the user positions their arm. Designation of privacy regions may change based on context and/or user position. For example, the size and positioning of a private sub-region may rotate away from other viewers and towards the body of the user dynamically based on the user's movement and/or positioning (e.g., walking, sitting, or driving). The device may include self-learning features in order to customize the size and positioning of the private and public sub-regions for each user based on, for example, the size and positioning of the user's arms. Privacy permissions can also be dynamic based on the physical location of the device, with privacy thresholds being lowered when a user is at home, or in another location designated as private or semi-private, such as an office or a vehicle.

Figure 9A:
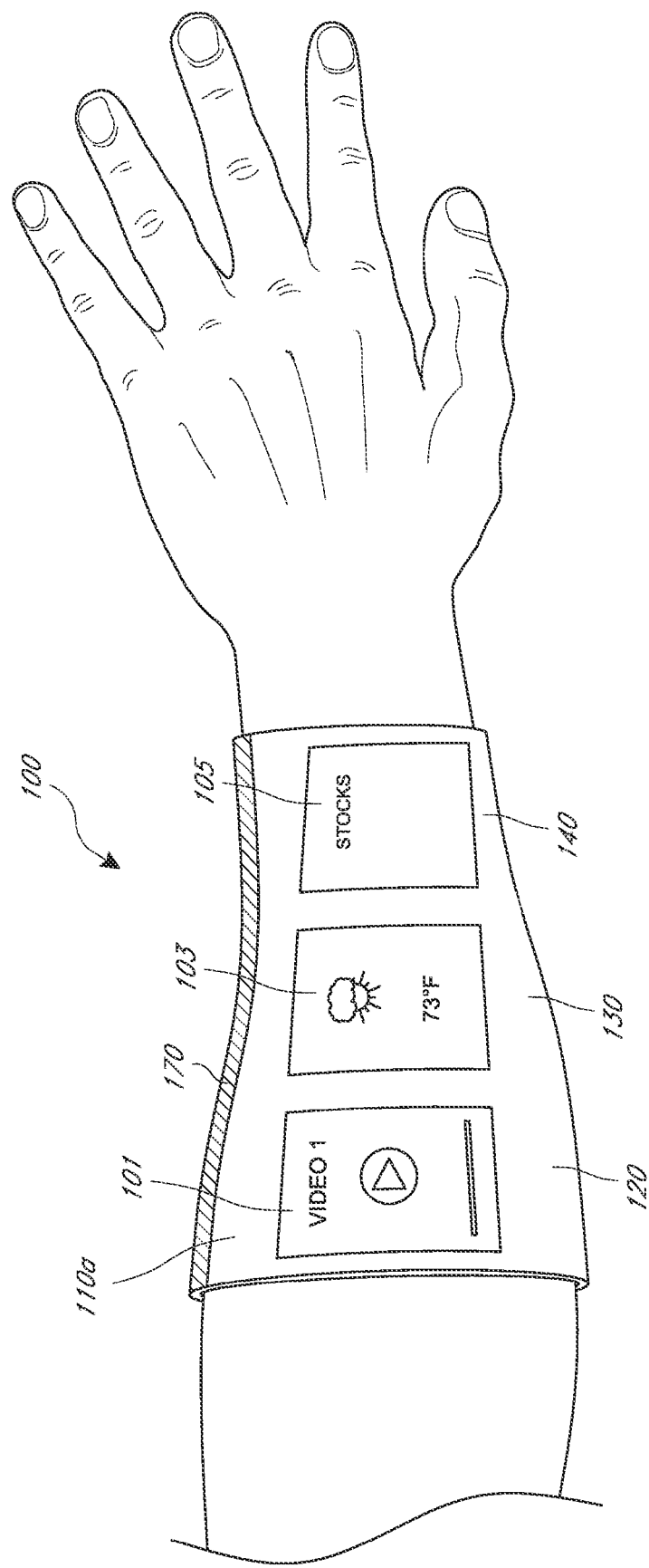
FIGS. 9A and 9B show an example of content display on a wearable device.
Figure 9B:
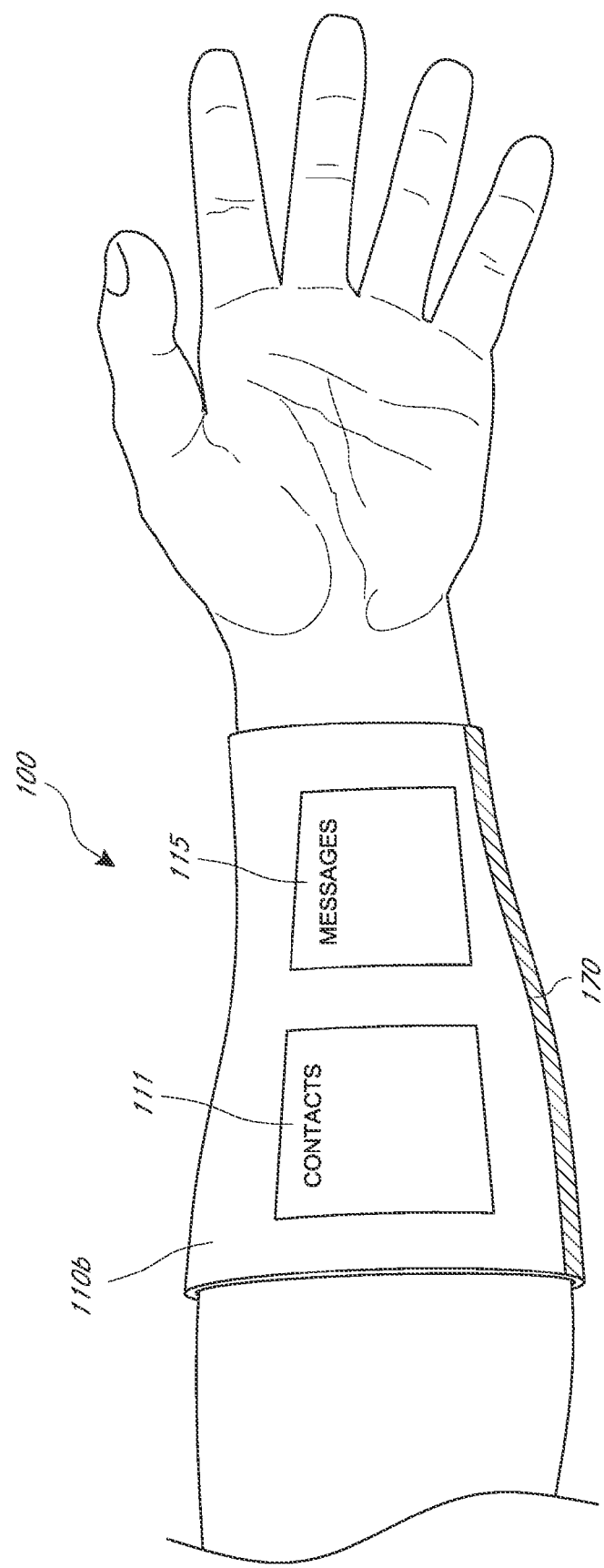

With reference to FIGS. 9A-9B, the display of public and private information on a wearable display device 100 is illustrated. FIG. 9A illustrates a top side view of the wearable display device 100 having a public display region 110a. FIG. 9B is a bottom side view of FIG. 9A and illustrates a bottom side view of the wearable display device 100 having a private display region 110b. As such, in the illustrated implementation, the wearable display device 100 includes a top side that is designated for the display of public information and a bottom side that is designated for the display of private information. In general, the public display area faces away from the user while the private display area faces towards the user's body so that it is difficult for people other than the user to see.

Continuing with FIGS. 9A-9B, the wearable display device 100 may include an inactive region 170. The inactive region 170 may be less flexible than the display areas. The inactive region 170 may provide a space for components other than the display. For example, the inactive region 170 may include batteries, processors, sensors, memory, antenna, and the like. As shown, the inactive region 170 is located along a narrow section on the lower and/or underside of the wearable display device 100 when a user's palm is facing up (as shown in FIG. 9B) as this portion of the wearable display device 100 is less visible from the point of view of the user when the device is worn. However, the inactive region 170 may be placed anywhere on the wearable display device 100 more than one inactive region 170 may be included. In some implementations, wearable display device 100 does not include an inactive region 170.

As shown in FIG. 9A, the public display region 110a is subdivided into three display regions 120, 130, and 140. As discussed above, the three display regions 120, 130, and 140 may be capable of displaying various image qualities that may be the same or different from region to another. In some implementations, the three display regions 120, 130, and 140 may be capable of being driven differently to provide varying image qualities across the public display region 110a. As shown, video content 101 from a first application is being displayed in display region 120, image data from a second application in the form of weather information 103 is being displayed in display region 130, and image data from a third application in the form of stock market information 105 is being displayed in display region 140. More or less than three display regions may be employed.

As shown in FIG. 9A, the private display region 110b is located on the underside of the wearable display device 100 and includes two display regions 160 and 180. More or less than two display regions may be employed. Display regions 160 and 180 may be capable of displaying various image qualities that may be the same or different from region to another. In some implementations, the two display regions 160 and 180 may be capable of being driven differently to provide varying image qualities across the private display region 110b. As shown, image data in the form of personal contacts 111 is being displayed in display region 160 and image data in the form of personal messages 115 is being displayed in display region 180.

The wearable display device 100 may be configured such that the wearable display device 100 can determine the orientation of the wearable display in space. For example, the wearable display device 100 may include one or more sensors. The one or more sensors may include may include, for example, motion sensors, accelerometers, gyroscopes, light detectors, gaze detectors, thermal sensors, deformation sensors, pressure sensors, cameras, and the like. In some implementations, the sensors are disposed within the inactive region 170. In some implementations, the sensors are embedded into portions of the display regions. The sensors may be configured to provide information regarding the positions of the display regions 120, 130, 140, 160, 170 and/or information regarding the positions of the public display region 110a and/or the private display region 110b.

In some implementations, the sensors can be used in determining which portions of the wearable display device 100 are facing towards a user and which portions are facing away from the user. For example, while FIGS. 9A-9B illustrate the private display region 110b generally located on the palm up facing side of the wearable display device 100 and the public display region 110a generally located on the palm down facing side of the wearable display device 100, the private display region 110b and the public display region 110a may switch positions as the wearable display device 100 is rotated. In other words, when the wearable display device 100 is moved in space with respect to the user, orientation of the private display region 110b and the public display region 110a may be changed. In some implementations, the wearable display device 100 is configured to display more private information on display regions facing toward a user's body and less private information on display regions facing away from the user's body. The wearable display device 100 may include one or more processors that are electronically coupled to one or more sensors. In some implementations, the processor(s) is configured to select where content is to be displayed on the wearable display device 100.

In some implementations, the wearable display device 100 is configured such that when the private display region 110b is moved such that it is facing away from the user and/or is moved to a position where the user cannot visualize the private display region 110b and/or when the private display region 110b is moved such that someone other than the user may visualize the private display region 110b, the private display region 110b is inactivated. In some implementations the wearable display device 100 is configured such that the private display region 110b is resized and/or reshaped in response to information provided by the one or more sensors of the wearable display device 100.

Figure 10A:
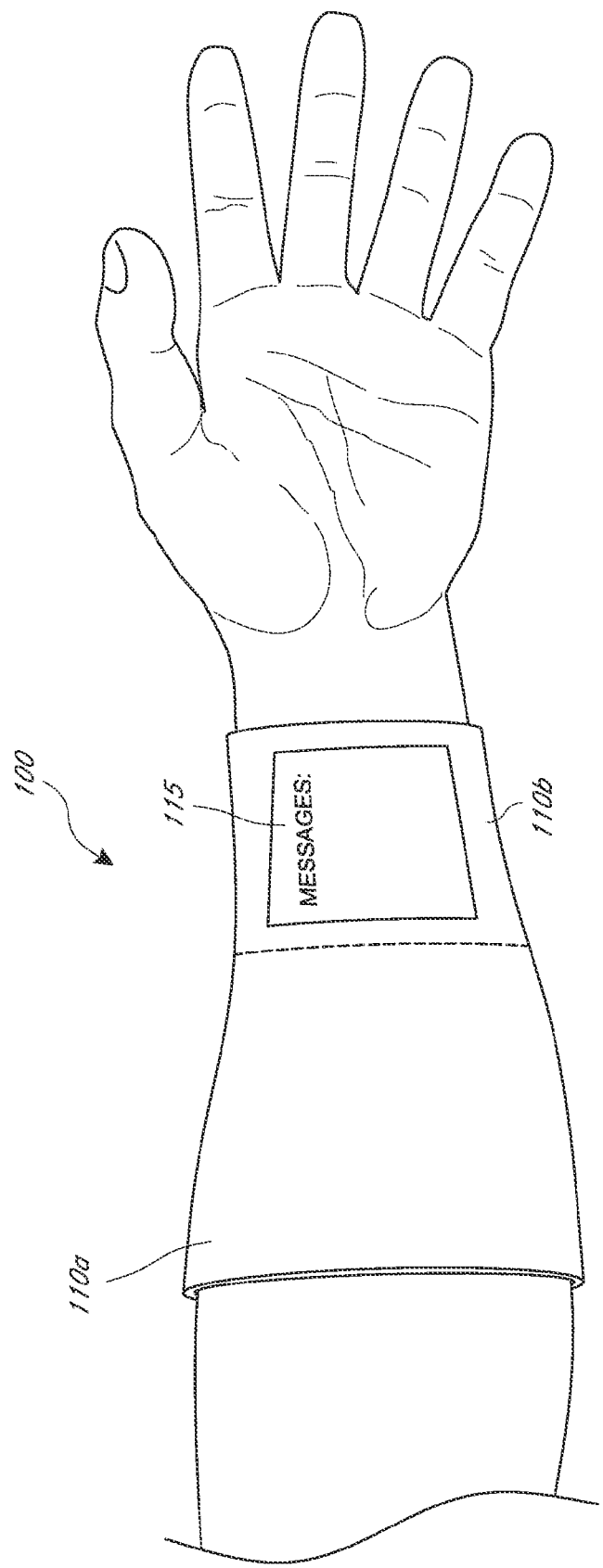
FIGS. 10A and 10B show another example of content display and reorganization on a wearable device.
Figure 10B:
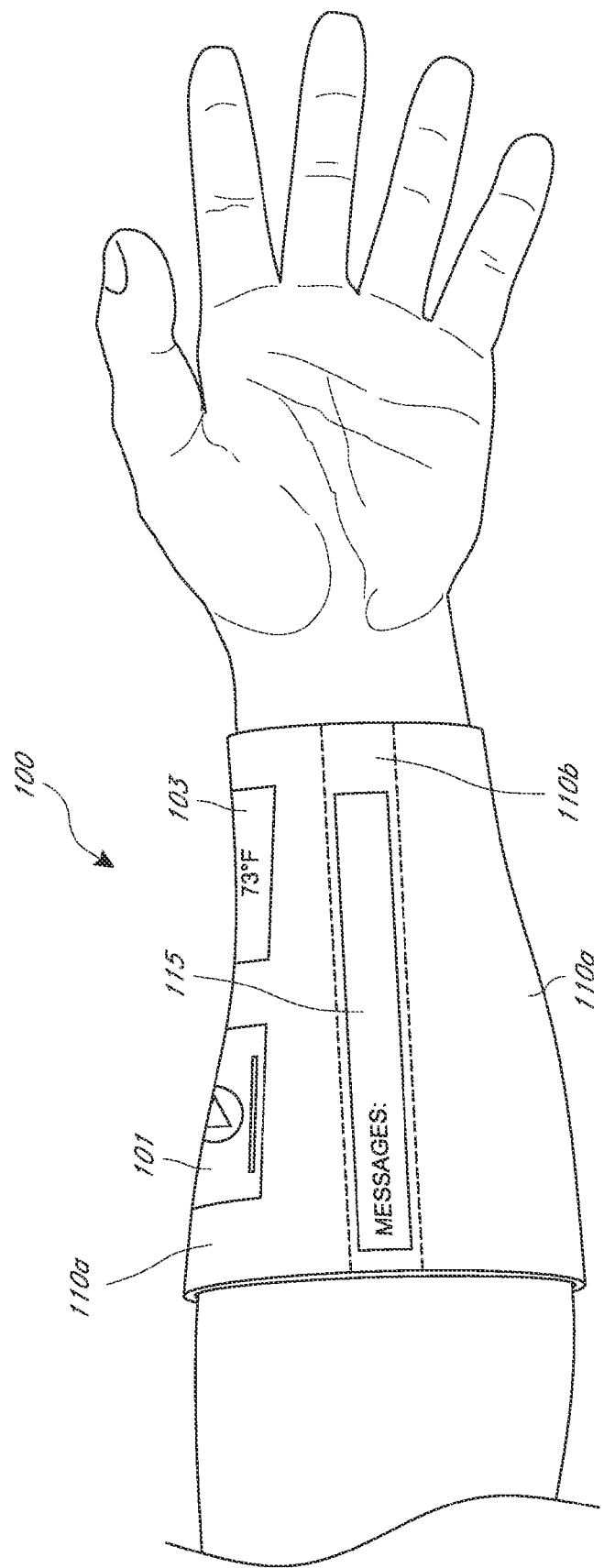

FIGS. 10A-10B illustrate the display of public and private information on a wearable display device 100 according to another implementation. As shown in FIG. 10A, the private display region 110b may be located in a generally rectangular area overlapping a user's inner wrist. The public display region 110a may encompass the remainder of the display area. In another implementation, shown in FIG. 10B, the private display region 110b may be located along a relatively thin and rectangular strip extending over a user's inner forearm while the public display region 110a encompasses the remainder of the display area. The relative size and/or positioning of the public and private display regions 110a, 110b may be fixed.

In other implementations, the relative size and/or positioning of the public and private display regions 110a, 110b is dynamic. For example, as shown in FIGS. 10A-10B, the private display region 110b may be resized and reshaped is response to additional content displayed on the public display region 110a. In FIG. 10A, personal messages 115 is being displayed within the private display region 110b and no content is being displayed in the public display region 110a. In FIG. 10B, the private display region 110b is resized and reshaped after video content 101 and weather content 103 are displayed within the public display region 110a.

Figure 11A:
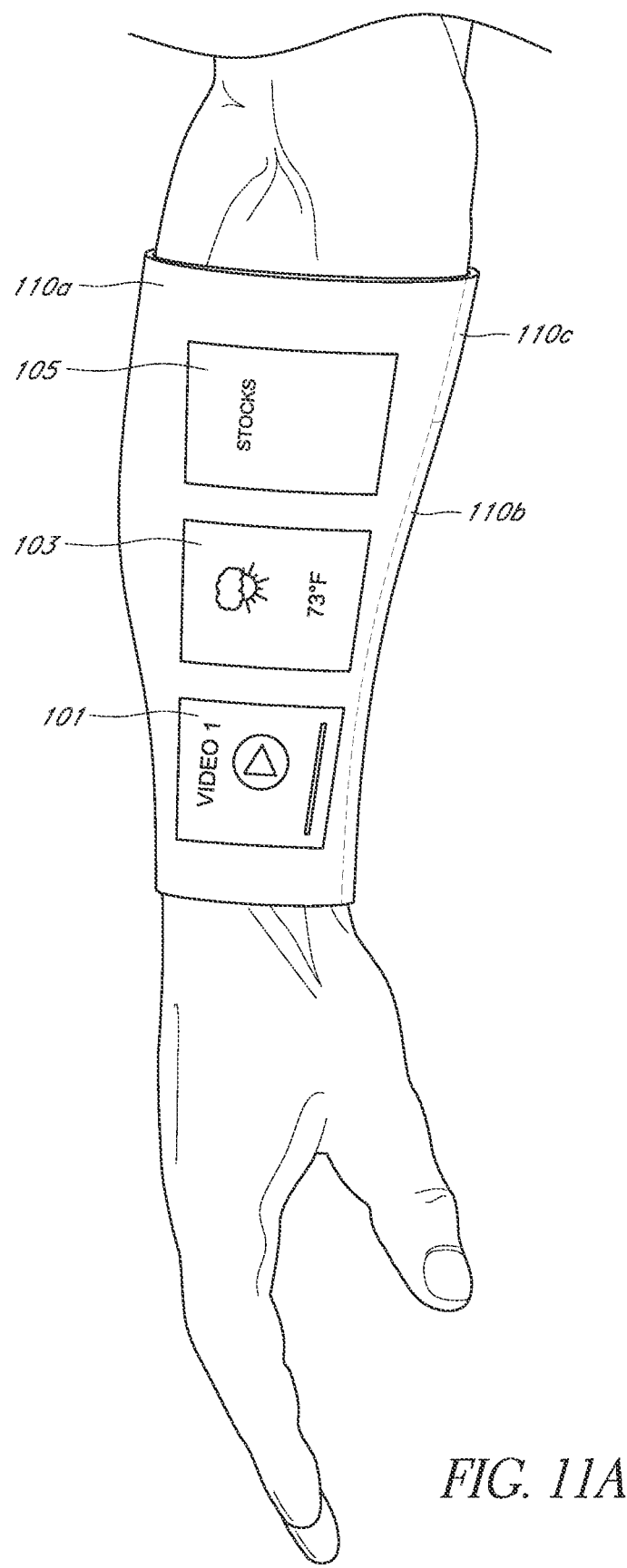
FIGS. 11A and 11B show another example of content display on a wearable device.
Figure 11B:
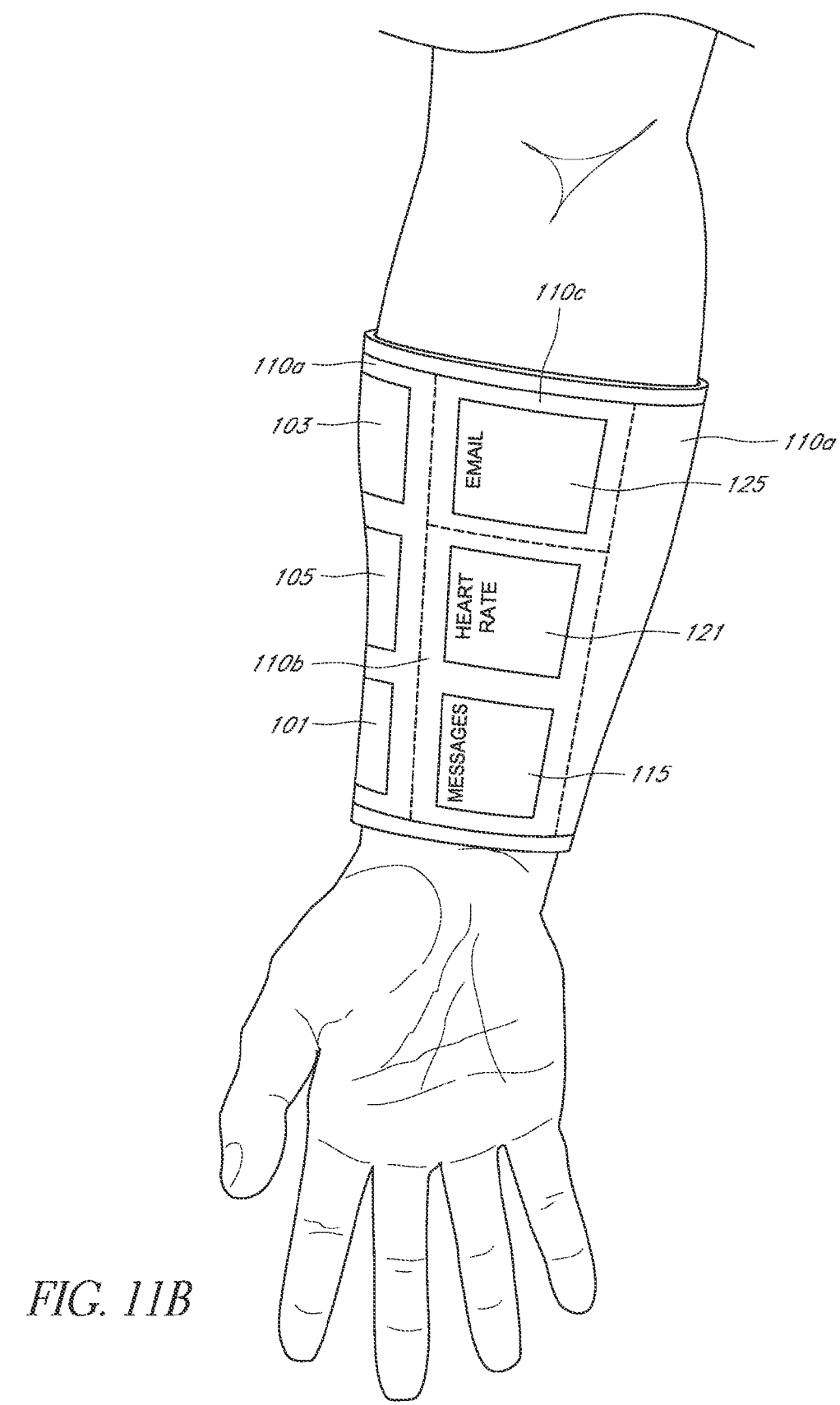

FIGS. 11A-11B illustrate the display of public, private, and semi-private information on a wearable display device 100 according to another implementation. FIG. 11A shows a side view of the wearable display device 100 being worn by a user. FIG. 11B illustrates the wearable display device 100 of FIG. 11A in a position where the user's arm has been rotated approximately 90° such that the user's palm is facing upward, exposing the underside of the wearable display device 100. As shown, in FIGS. 11A and 11B, the public display region 110a extends around the outside of the user's forearm, while the private display region 110b and semi-private display region 100c are located along the inside of the user's forearm. The private display region 110b may be generally disposed over the user's inner wrist, while the semi-private region 110c may be located along the inner forearm of the user; distal to the wrist and the private display region 110b. Public content such as, for example, video content 101, weather content 103, and stock content 105 may be displayed within the public display region 110a. Private content such as, for example, personal messages 115 and health information 121 may be displayed within the private display region 110b. Semi-private content such as, for example, email content 125 may be displayed within the semi-private display region 110c.

The boundaries of the public display region 110a, private display region 110b, and/or semi-private display region 110c may be fixed and/or dynamic. In other words, the various display regions within the display may be fixed sizes and shapes and or the sizes, shapes, and orientations may change during use. In some implementations, the boundaries may be resized, reshaped, or reoriented in response to information provided by one or more sensors. For example, the boundaries may be determined and or altered based at least in part on the orientation of the wearable display device 100. In some implementations, the boundaries may be determined and or altered based at least in part on the amount content that is to be displayed. For example, the size of the private display region 110b may increase if a user wishes to view a large amount of private information or may shrink and/or may no longer be displayed if the user wishes to display less private content or does not wish to display any private content.

The relative privacy level of content may be user selected. In other implementations, a processor may be configured to determine a privacy level of the content. The privacy level may be based in part on one or more of, for example, user input, the application that wishes to display content, the file extension, the type of media. In some implementations, the processor may compare one or more aspects of the display data from one or more applications and determine the optimal sub-regions for displaying the data based at least in part on the privacy level of the content.

As shown in FIGS. 12A-12D, the wearable display device 100 may interact with a complementary device 200. As illustrated, and similar to the implementation shown in FIGS. 9A-9B, the wearable display device 100 includes a private display region 110b generally located on the palm up facing side of the wearable display device 100, a public display region 110a generally located on the palm down facing side of the wearable display device 100, and an inactive region 170 located along an section of the wearable display device 100 extending along the underside of the user's forearm.

Figure 12A:
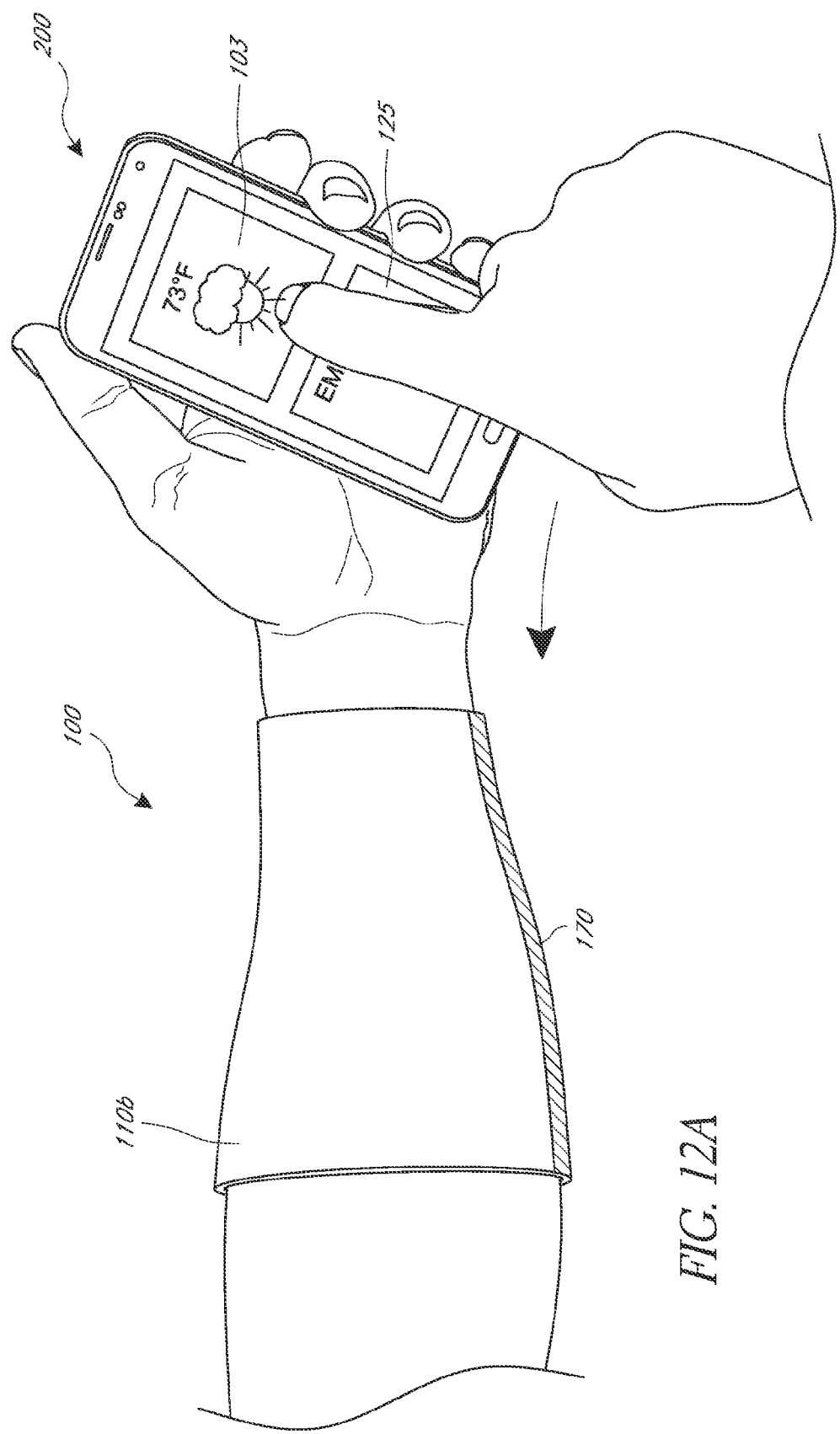
FIGS. 12A-12D show another implementation in which a mobile phone serves as a complementary device for a wearable display device.

FIGS. 12A-12D illustrate an example implementation of the wearable display device 100 in use with a complementary device 200. As shown, the complementary device 200 may display multiple types of content at once. The complementary device 200 may include one or more applications that are used to display content. In FIG. 12A, the complementary device is shown as displaying weather content 103 and email content 125. The weather content 103 may have a first associated privacy level and the email content 125 may have a second privacy level. The privacy level may be predetermined or determined by a processor. The processor may be located within the complementary device 200 and/or within the wearable display device 100.

Figure 12B:
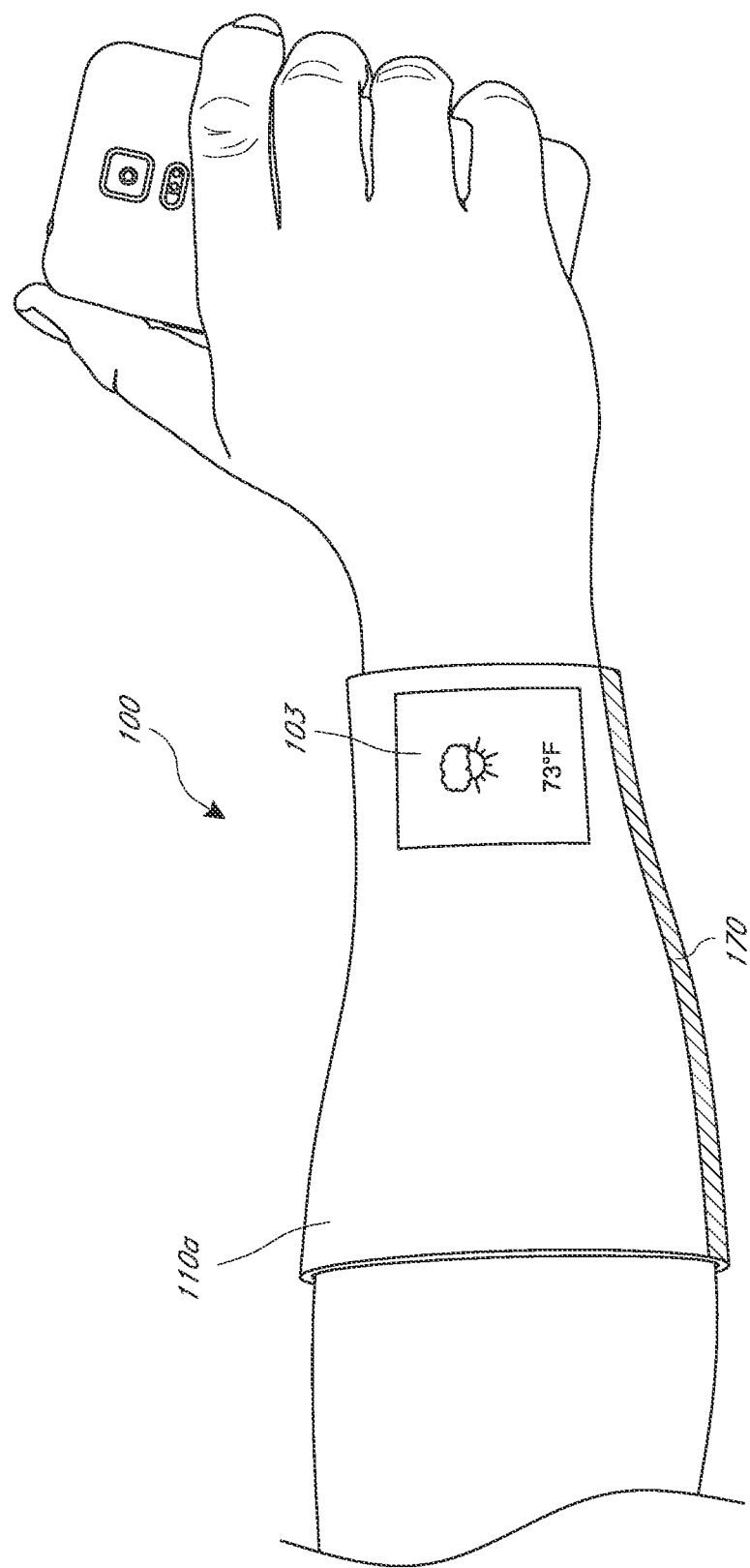

Continuing with FIG. 12A, the user may select the weather content 103 for display on the wearable display device 100. Thus, as shown, the user may select the weather content 103 by dragging and dropping the weather content 103 onto the wearable display device 100. The processor may direct the weather content 103 onto the public display region 110a as shown in FIG. 12B based at least in part on the privacy level associated with the weather content 103.

Figure 12C:
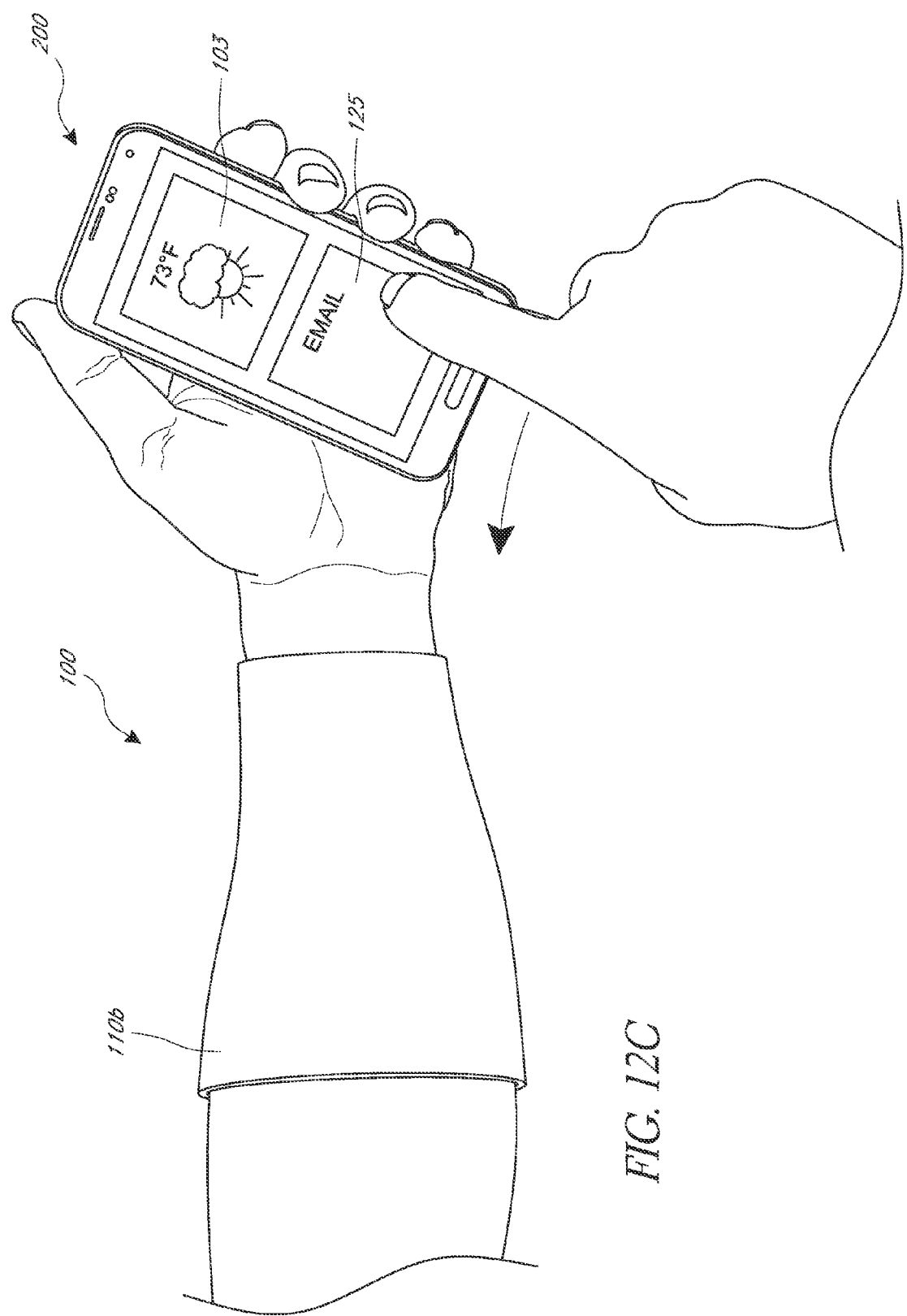
Figure 12D:
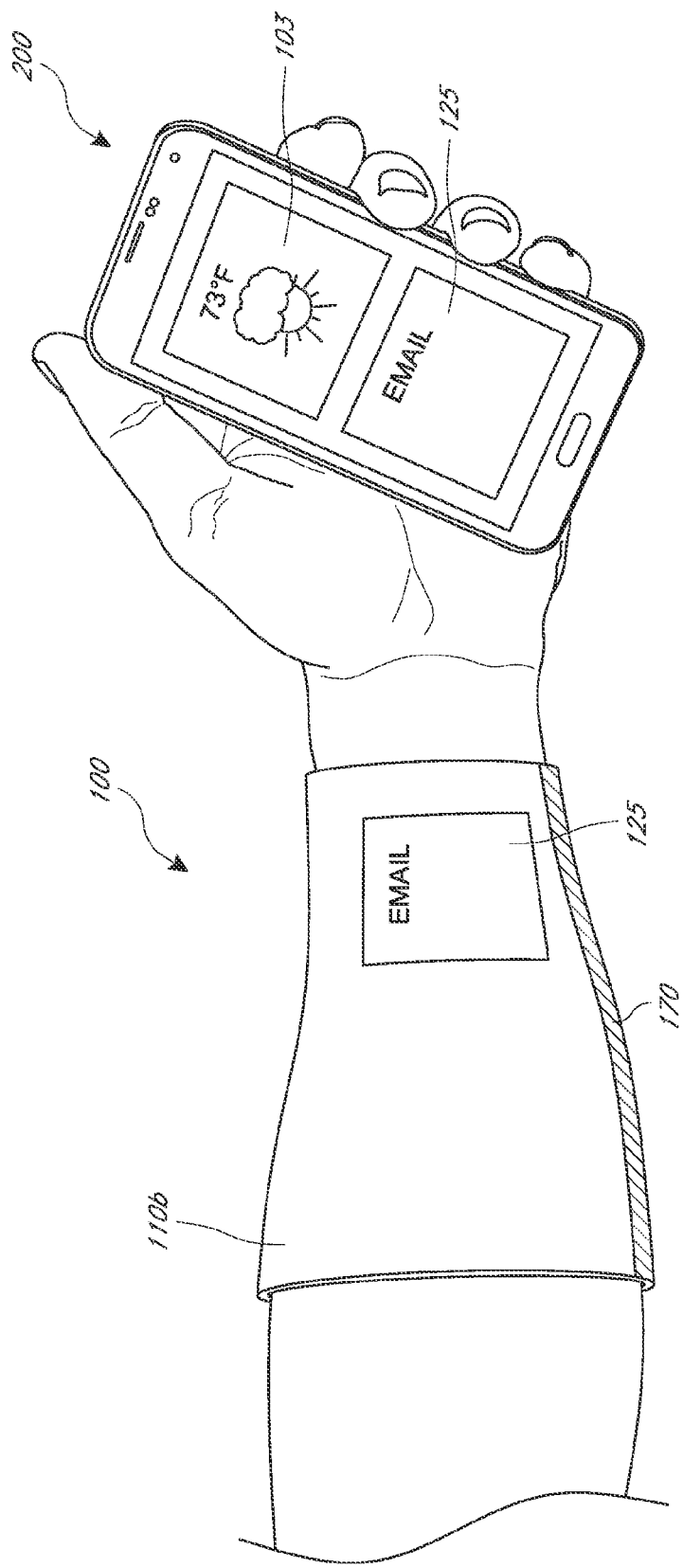

Turning to FIG. 12C, the user may select the email content 125 for display on the wearable display device 100. Thus, as shown, the user may select the email content 125 by dragging and dropping the email content 125 onto the wearable display device 100. The processor may direct the email content 125 onto the private display region 110b as shown in FIG. 12D based at least in part on the privacy level associated with the email content 125.

Figure 13:
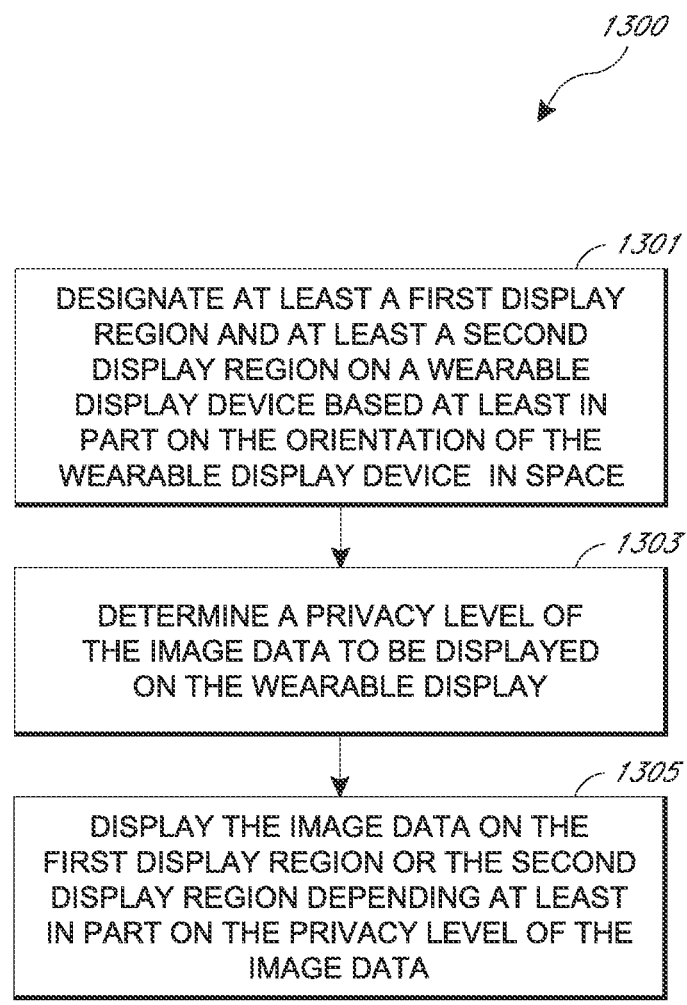
FIG. 13 is a flow diagram illustrating an example method for displaying content in display regions of a wearable display device.

FIG. 13 is a flow diagram illustrating an example method 1300 for displaying content in display regions of a wearable display device 100. The method 1300 may include a first block 1301 in which at least a first display region and at least a second display region are designated on a wearable display device such as the wearable display device 100 of FIG. 1. The first and second regions may be sub-regions within a larger display area, such as the display area 110 of FIG. 1. The first display region and the second display region may be designated based at least in part on the orientation of the wearable display device in space. In some implementations, the first display region is located in a location on the wearable display device that cannot be seen by a person who is not wearing the device.

In some implementations, the method 1300 may optionally include a determination of the position of the wearable display device, such as a determination as to how the wearable display device is oriented in space. The designation of the first and second display areas may be based at least on part on the orientation of the wearable display, and the method 1300 may in some further implementations optionally include periodically adjusting the location and/or boundaries of the first and second display regions during use based at least on part on determinations of the orientation of the wearable display. For example, the method 1300 may optionally include designating a region of a display area that faces a user's body as the first display region and designating a region of a display area that faces away from a user's body as the second display region. In some implementations, the designation of the first and second display areas may be based at least on part on the location and degree of deformation of the wearable display, and the method 1300 may in some further implementations method 1300 may optionally include adjusting the location and/or boundaries of the first and second display regions during use based at least on part on the location and degree of deformation of the wearable display.

The method 1300 may then move to block 1303, at which a privacy level associated with the image data to be displayed on the wearable display device is determined. Although illustrated in FIG. 13 as occurring after the designation of at least a first display region and at least a second display region at block 1301, the determination of a privacy level associated with the image data to be displayed can be determined prior to or simultaneously with the designation of the first display region and the second display region.

The method 1300 may then move to block 1305 at which the image data is displayed on at least one of the first or second display regions, depending at least in part on the privacy level associated with the image data to be displayed on the wearable display device. Some or all of the blocks of method 1300 may be performed repeatedly during use of the wearable display device, and may be triggered, for example, at preset intervals, by user input, or by movement of the wearable display device.

With reference now to FIGS. 14A-16B, in some implementations, the wearable display devices 100 disclosed herein include a plurality of deformation sensors configured to determine and/or monitor the state of the flexible display. In some implementations, the sensors may be configured to detect physical deformation of the wearable display device 100. For example, the sensors may be configured to detect deformation or distortion of the display, such as crimps, folds, wrinkles, and/or stretched areas of the display. The deformation sensors may in some implementations be pressure sensors, although other appropriate types of sensors may also be used. For example, the sensors could include force collection sensors, piezoresistive strain gauges, capacitive type sensors, electromagnetic sensors, piezoelectric sensors, optical sensors, potentiometric sensors, and the like.

In response to sensor output, at least one characteristic of the display may be changed. The characteristic of the display may include the brightness, size, shape, resolution, and the like. In other words, the wearable display device 100 may be able to identify deformation of the display or determine the physical shape of the display and adjust the displayed content accordingly.

Figure 14A:
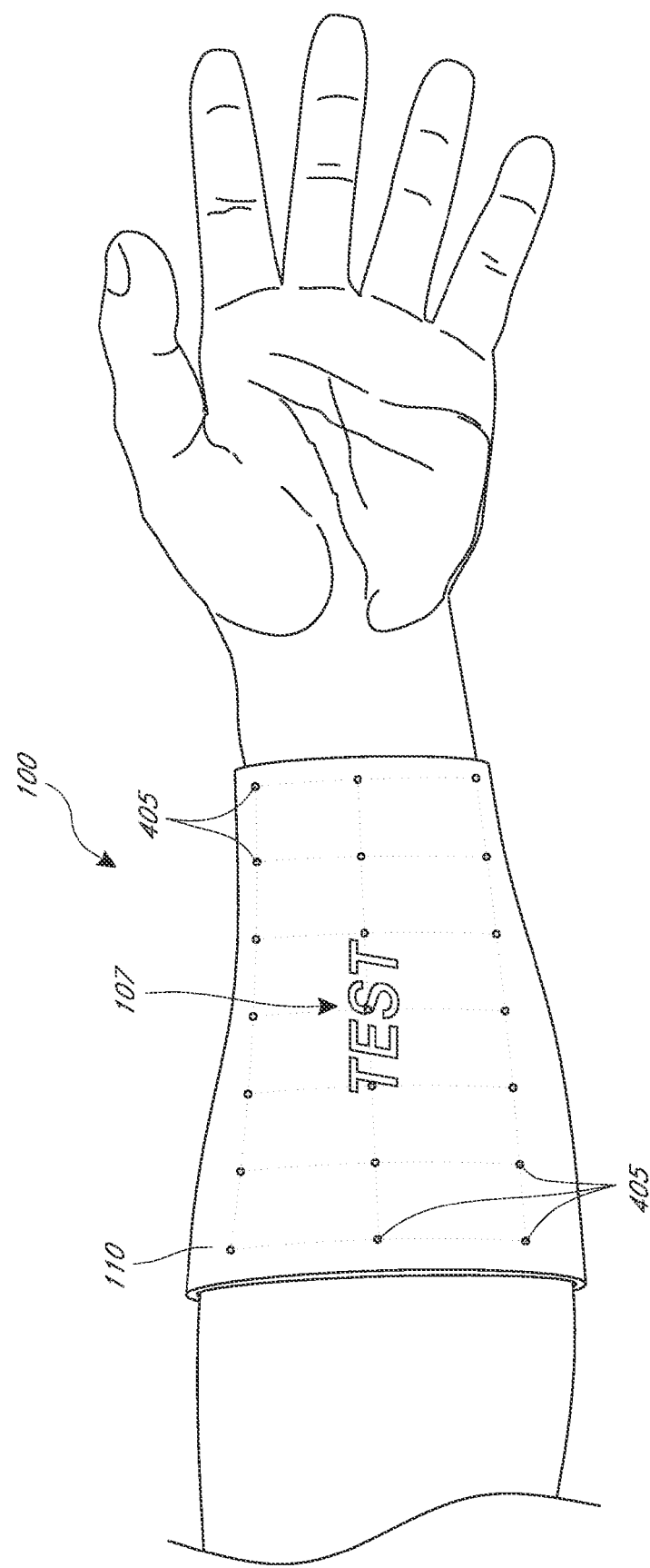
FIGS. 14A-14C show an implementation of a wearable device having a plurality of deformation sensors.
Figure 14B:
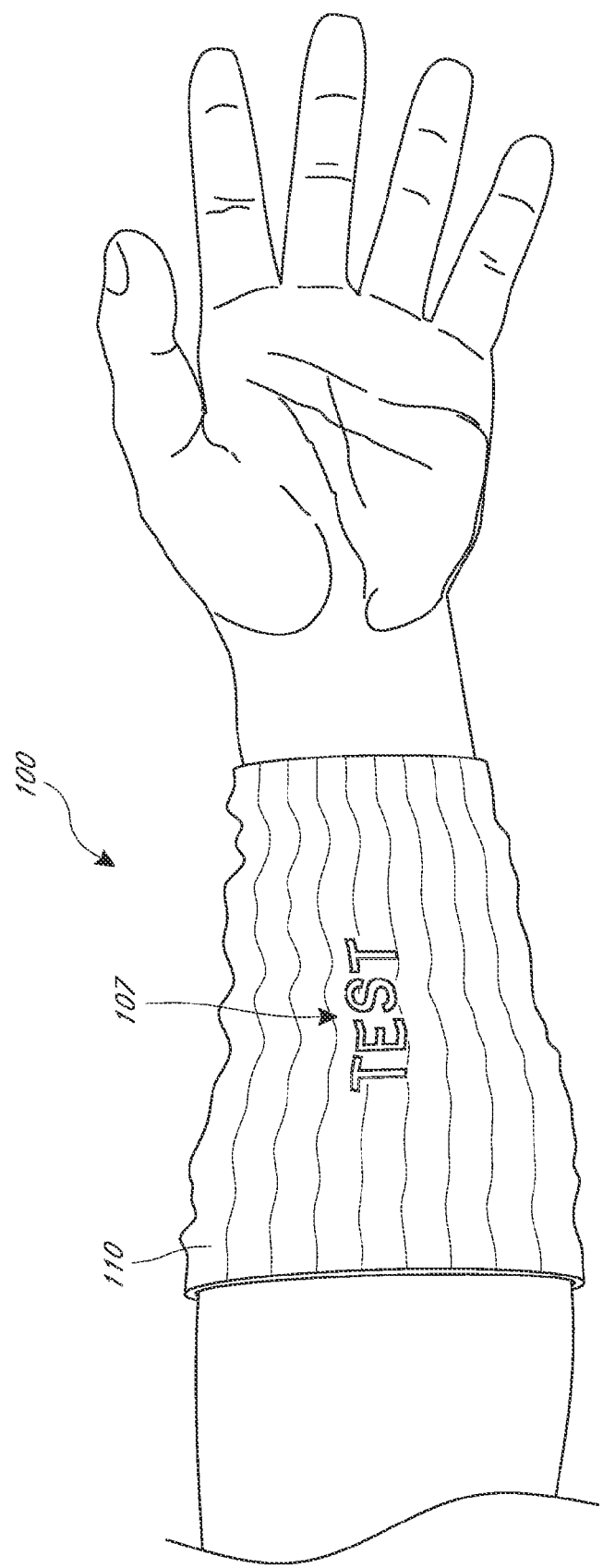
Figure 14C:
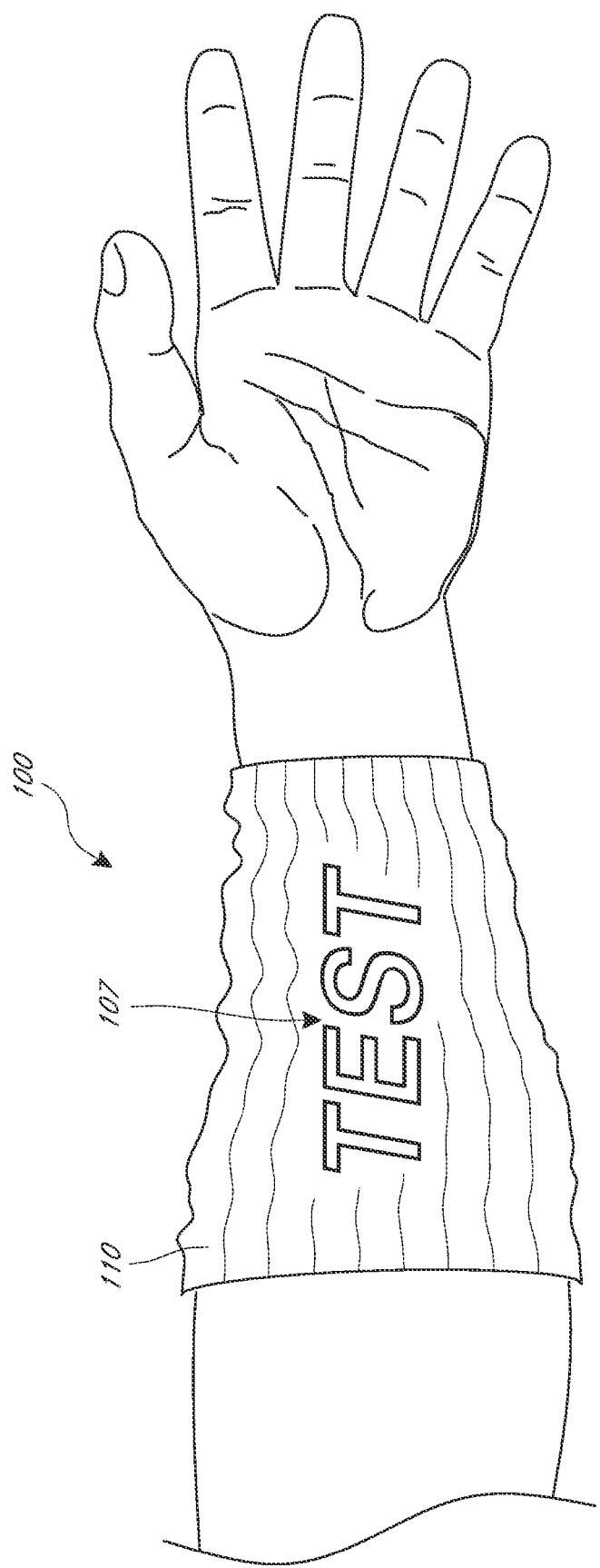

As shown, for example, in FIGS. 14A-14C, the size of the text or other display elements may be increased when the wearable display device 100 is deformed. FIG. 14A illustrates a plurality of deformation sensors 405 embedded within a grid-like pattern within the display 110. The deformation sensors 405 may be in electrical communication with one or more processors. As shown in FIG. 14A, text content 107 is being displayed on the display 110.

While the deformation sensors 405 are illustrated in a grid-like pattern, any suitable arrangement of deformation sensors 405 may be employed. More or less sensors than shown may also be included. In some implementations, the deformation sensors 405 include one or more pressure sensors. In some implementations, the wearable display device 100 includes a pressure membrane disposed within at least a substantial portion of the wearable display device 100. Information from the pressure membrane may be used at least in part to determine the relative level of folding or wrinkling across the wearable display device 100. For example, wherever there is a fold or wrinkle, the local pressure will increase due to the structure of the membrane pushing against itself. In this way, the location and degree of relative wrinkling of one or more sections of the wearable display device 100 may be determined.

Turning the FIG. 14B, the wearable display device 100 is shown in a deformed state. That is to say, the wearable display device 100 includes a plurality of folds or wrinkles which may tend to obscure and/or impair the readability of the text content 107. The level of folding and/or wrinkling may be determined at least in part by one or more of the plurality of deformation sensors 405. In response to the information provided by the deformation sensors 405, the processor may change at least one characteristic of the displayed text content 107. In some implementations, the processor is configured to adjust at least one image characteristic of the displayed content in response to signals indicating that the relative deformation has exceeded one or more threshold levels. For example, as shown in FIG. 14C, in response to the deformation, the size of the text content is increased. The increase in text size may allow for the text content to be read by a user even when the wearable display device 100 is in a deformed state. In another example, in response to the deformation, the size of the icons displayed on the wearable display device 100 is increased. In another example, in response to the deformation, the image resolution displayed on the wearable display device 100 is adjusted.

Figure 15A:
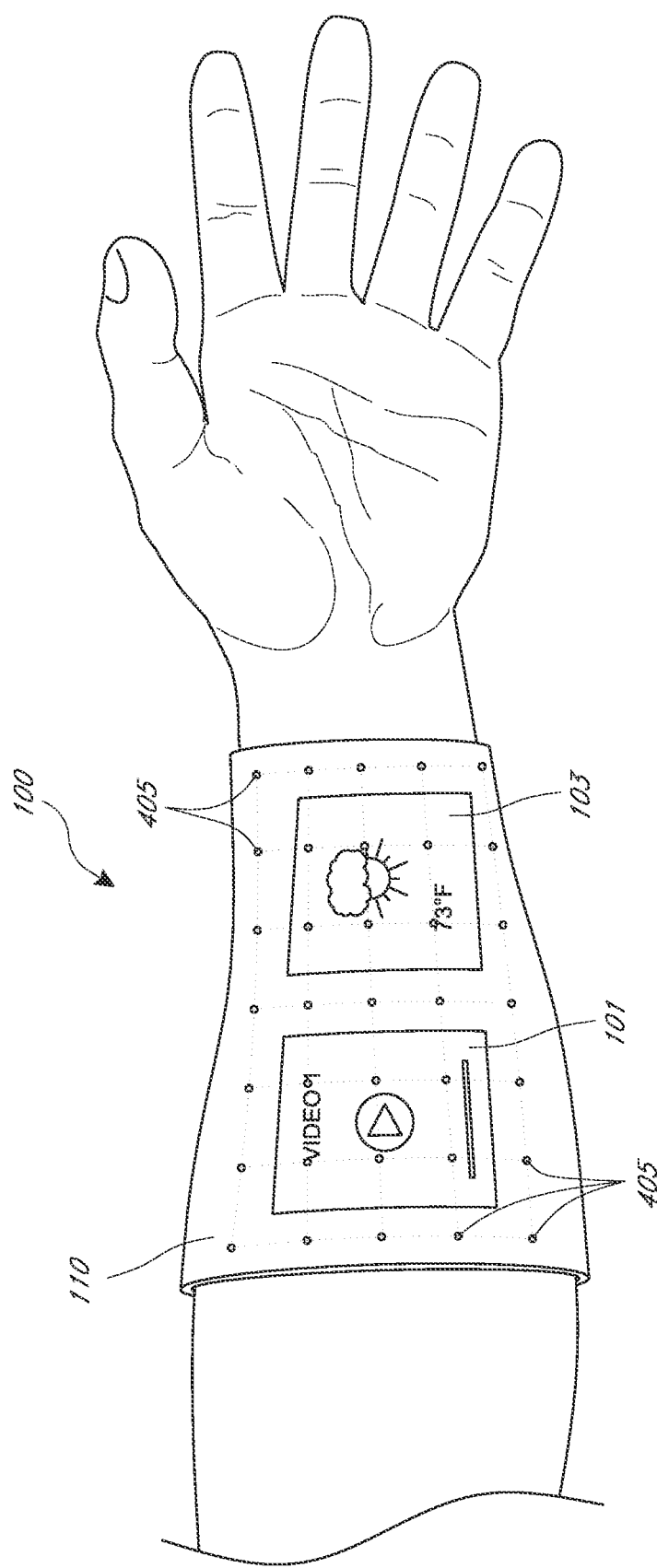
FIGS. 15A-15B show an example of content display and reorganization on a wearable device having a plurality of deformation sensors.
Figure 15B:
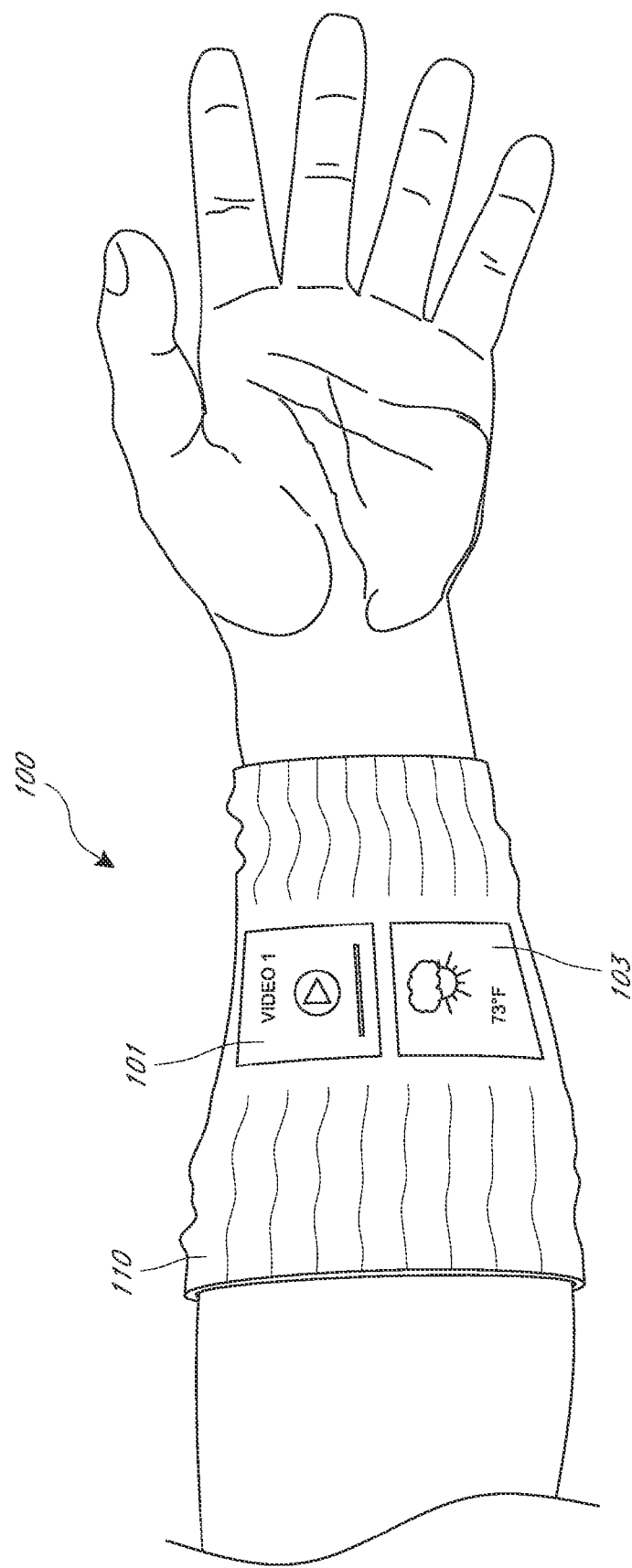

In another implementation, shown for example in FIGS. 15A-15B, the processor may resize and/or reshape displayed content in response to information received from one or more deformation sensors 405. FIG. 15A illustrates the side-by-side display of video content 101 and weather content 103 on the display area 110 of the wearable display device 100. FIG. 15B is the same as FIG. 15A expect that the distal and proximal ends of the wearable display device 100 are deformed. In response, the video content 101 and weather content 103 are moved and resized such that they are located in an area of the display 110 that is less deformed. In this way, the video content 101 and weather content 103 can be more easily viewed by a user. That is to say, as wrinkles obstruct one or more portions of the display, the effective resolution may become less, and in response, the wearable display device 100 may automatically re-scale content (e.g., photos and videos) to fit within the remaining pixels rather than be cropped or obscured.

Figure 16A:
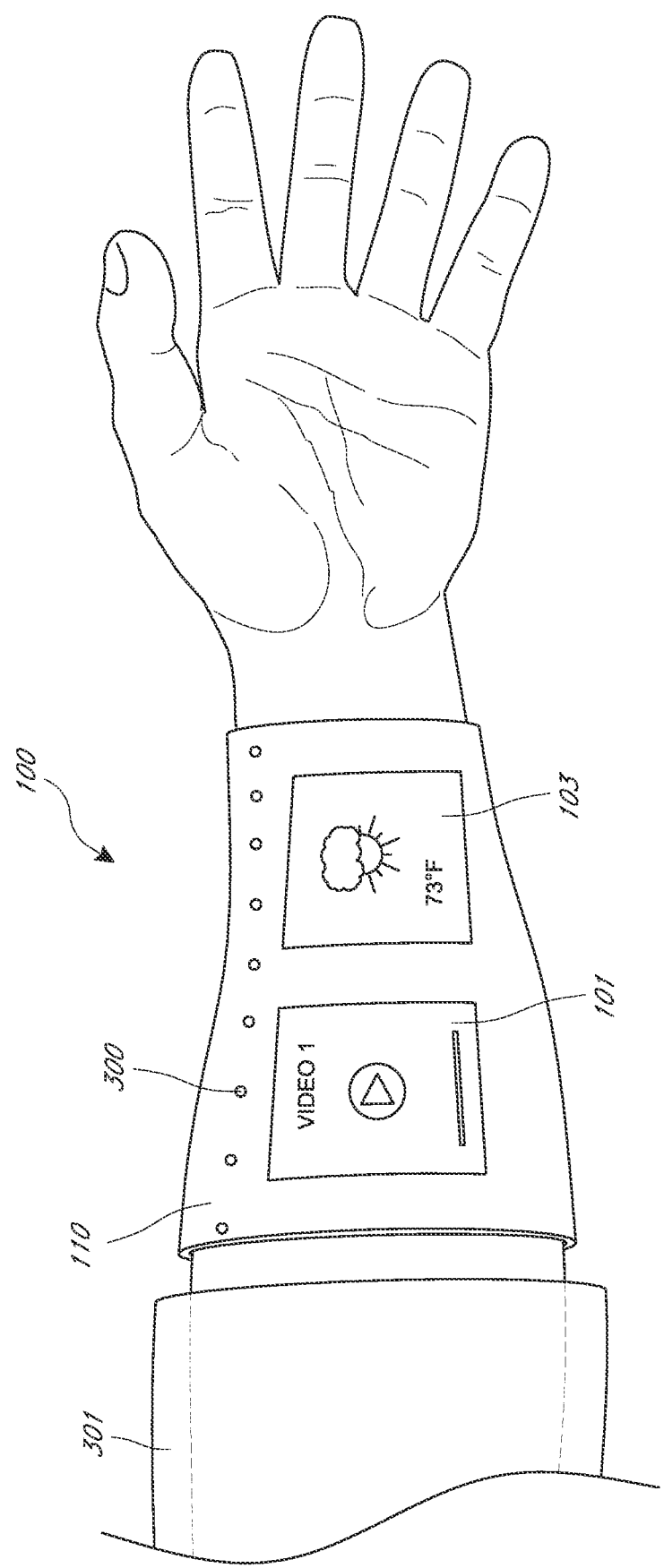
FIGS. 16A-16B show an implementation of a wearable device having a plurality of light sensors.
Figure 16B:
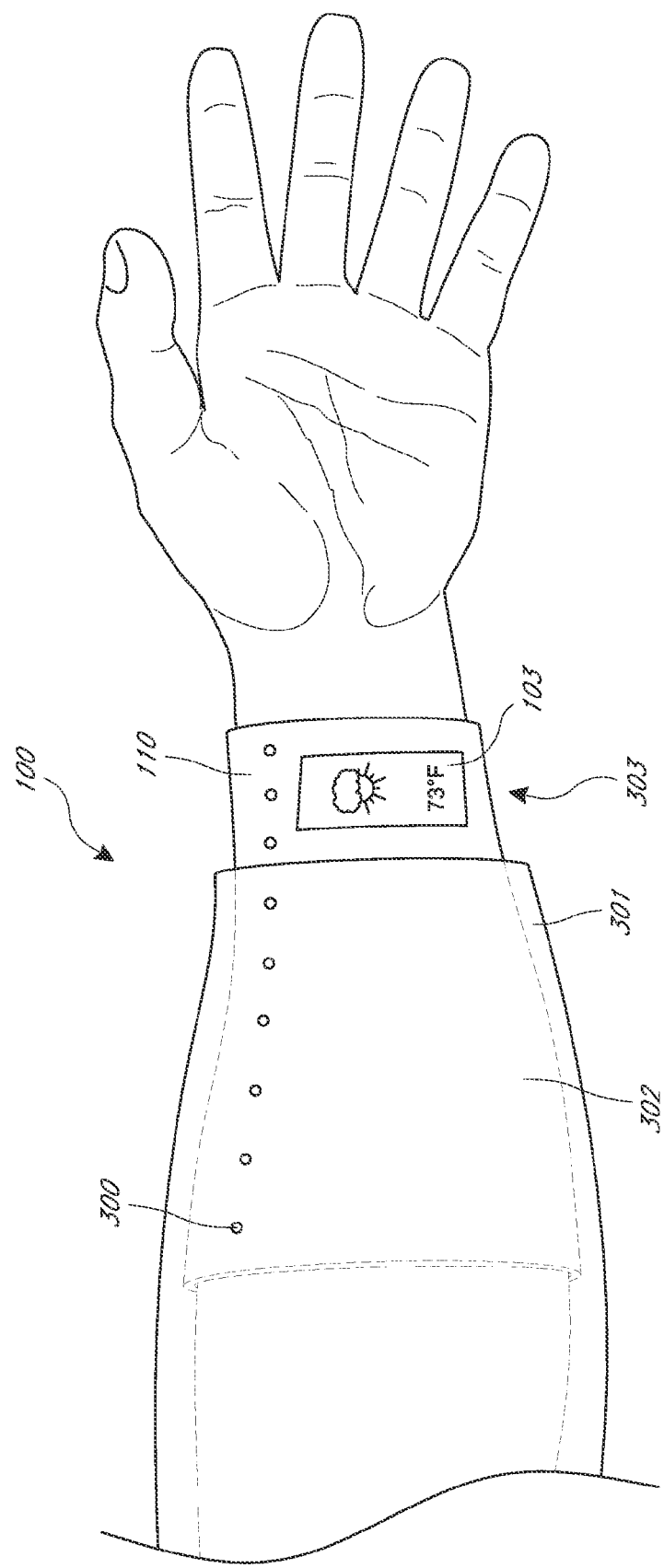

In another implementation, as shown for example in FIGS. 16A-16B, the wearable display device 100 may include sensors 300 configured to detect light. In some implementations the sensors may be configured to detect ambient light. Thus, when the wearable display is partially or fully covered, by a shirt sleeve for example, the regions of the display that do not detect incident light can be deactivated in order to conserve power. In other words, a user may wish to cover a portion or the entirety of the wearable display, with for example a sleeve of an article of clothing, when the user is not using the wearable display device 100. These covered portions of the wearable display device 100 may be deactivated and/or powered off automatically. That is to say, less than the entire wearable display device 100 may be driven when it is determined that less than the entire wearable display device 100 display is visible to the user.

In particular, FIG. 16A illustrates a wearable display device 100 which includes sensors 300 disposed at various locations across the surface of the wearable display device 100 and configured to detect light. The sensors 300 may in some implementations include photodiodes, but may also include any other components suitable for detection of light. In FIG. 16A, the wearable display device 100 is not covered by the user's sleeve 301. In FIG. 16B, the user's sleeve has been pulled down the user's forearm so as to partially obscure the wearable display device 100. An obscured portion 302, may be deactivated or powered off automatically, or may be driven at a lower image quality, such as a lower brightness, when the portion 302 of the wearable display device 100 is obscured. The unobscured portion 303 may be driven as normal, or may be adjusted to compensate for the deactivation of obscured portion 302.

The portion of the wearable display device 100 which remains active can be reorganized to display all or a portion of the content previously displayed on the deactivated portion. For example, the content can be reduced in size and rearranged so that all of the image content previously being displayed on the wearable display device 100 is still being displayed on the smaller active area of the wearable display device 100. In FIG. 15B it can be seen that the video content 101 is no longer being displayed, and the weather content 103 has been resized to fit within the active area of the devices. In other implementations, content having a higher priority can be moved to the active area of the display, such as the applications or other image data with which the user most recently interacted.

The deactivated portion of the wearable display device 100 need not correspond exactly with the obscured portion 302. When discrete portions of the wearable display device 100 are driven as discrete within the wearable display device 100, a partially obscured display region can remain active, be resized, or be deactivated. The treatment of a partially-obscured display region can be based, for example, on the degree to which that display region is obscured, or on user preferences.

In another implementation, the wearable display device 100 may include one or more proximity sensors. The proximity sensors may be configured to determine if the wearable display device 100 is covered by, for example, an article of clothing or otherwise obscured. As such, when the proximity sensors detect an object in close proximity to at least a portion of the display, that portion of the display may be deactivated in order to reduce power consumption.

It is also contemplated that the content displayed on the wearable display device 100 may be reorganized, resized, and/or reconfigured in response to information from the light sensors and/or proximity sensors. For example, displayed content from two applications may be displayed side-by-side on the wearable display device 100. A portion of the wearable display device 100 may be covered such that one of the two applications is covered as well. In turn, the displayed content may be resized to fit side-by-side on the uncovered portion of the wearable display device 100. In another implementation, the displayed content may be reorganized such that the content displayed by the two applications is shown as one content window on top of a second content window rather than side-by side in order to fit within the uncovered portion of the wearable display.

Figure 17:
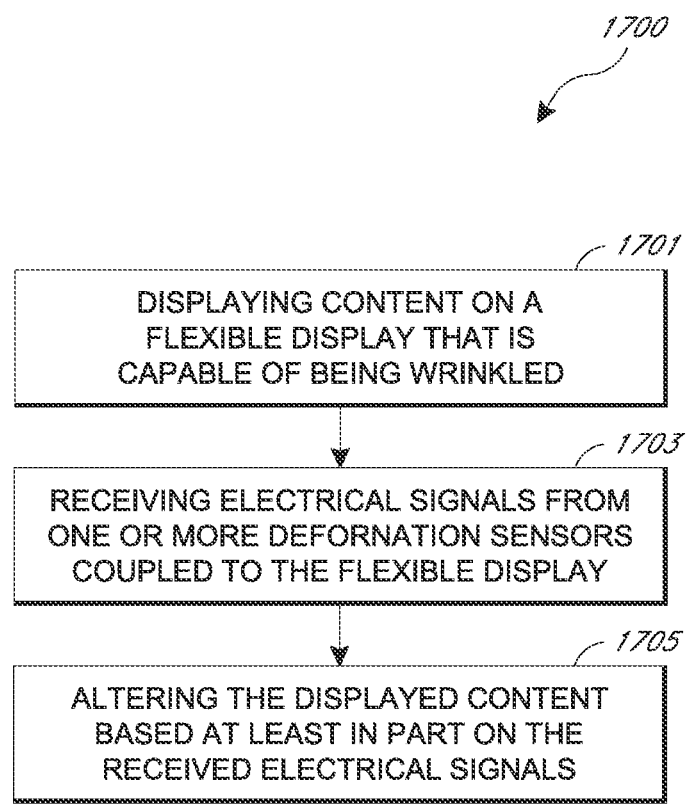
FIG. 17 is a flow diagram illustrating another example method for displaying content in display regions of a wearable display device.

FIG. 17 is a flow diagram illustrating another example method 1700 for displaying content in display regions of a wearable display device 100. The method 1700 may include a first block 1701 at which content is displayed on a flexible display that may be subject to wrinkling or similar deformation. The method 1700 can then move to block 1703 at which electrical signals are received from one or more deformation sensors coupled to the flexible display. The method 1700 can then move to block 1705 at which the displayed content is altered based at least in part on the received electrical signals. Altering the displayed content may include increasing a font size of text within the displayed content, reducing an area in which of the displayed content is displayed, and/or deactivating a portion of the flexible display.

Other implementations may utilize various combinations of content analysis, predefined preferences, or user input to reorganize displayed image data across multiple regions of a display. For example, in some implementations, image data being displayed in a particular display region may be expanded automatically or in response to user input to cover multiple display regions, or a display region may be dynamically subdivided into two sub-regions to effectively display image content. A variety of other combinations of the methods and components discussed herein are also possible.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, relative terms such as "upper" and "lower" are sometimes used for ease of describing the figures, and indicate relative positions corresponding to the orientation of the figure on a properly oriented page, and may not reflect the proper orientation of a particular component as implemented or during use.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A wearable display device, comprising:
   a display, the display including a first contiguous region of the display configured to display images at a first image quality and a second contiguous region of the display configured to display images at a second image quality; and
   a processor capable of:
      selecting a contiguous region of the display in which image data will be displayed based at least in part on the content of the image data; and
      displaying the image data in the selected contiguous region of the display.

2. The device of claim 1, wherein the display comprises a flexible display capable of operation over a range of curved states.

3. The device of claim 1, wherein displaying the content in the selected contiguous region of the wearable display device includes moving the display of content from one of the first or second regions to the other of first or second regions.

4. The device of claim 1, wherein the first contiguous region of the display and second contiguous region of the display can be dynamically resized.

5. The device of claim 1, wherein the processor is also capable of assigning an image quality for a contiguous region of the display.

6. The device of claim 1, wherein selecting a contiguous region of the display in which image data will be displayed is based at least in part on a priority of the image data.

7. The wearable display device of claim 6, wherein the image data priority is based at least in part on one or more user preferences associated with one or more user profiles.

8. The device of claim 7 wherein the processor is further capable of selecting the one or more user profiles based on biometric information indicative of a current user of the wearable device.

9. The device of claim 2, wherein the image data is provided by a software application, and wherein selecting the contiguous region of the display in which image data will be displayed is based at least in part on the software application providing the image data.

10. The device of claim 9, wherein the software application has a priority level associated therewith, and wherein selecting the contiguous region of the display in which image data will be displayed is based at least in part on the priority level.

11. The device of claim 9, wherein selecting a contiguous region of the display in which image data will be displayed is based at least in part on information relating to the usage history of the software application.

12. The device of claim 1, wherein selecting the contiguous region of the display in which image data will be displayed is based at least in part on a content type associated with the image data.

13. The device of claim 1, wherein the selection of the contiguous region of the display in which image data will be displayed is based at least in part on an image format associated with the image data.

14. The device of claim 1, wherein the first image quality is a first color gamut and the second image quality is a second color gamut that is broader than the first color gamut.

15. The device of claim 1, wherein the first contiguous display region has a first pixel density and the second contiguous display region has a second pixel density different than the first pixel density, and wherein selecting a contiguous region of the display in which image data will be displayed is based at least in part on a resolution of the image data.

16. The device of claim 1, wherein the first contiguous display region is configured to display image data at a first refresh rate and the second contiguous display region is configured to display image data at a second refresh rate different than the first refresh rate, and wherein selecting a contiguous region of the display in which image data will be displayed is based at least in part on a rate at which the image data will be refreshed.

17. A method of operating a wearable display device, the wearable display device having a display area having at least two contiguous sub-regions configured to display at least two different image qualities, the method comprising:
   receiving a command to display image data;
   selecting an appropriate contiguous sub-region of the display area for displaying the content based at least in part on the content of the image data; and
   displaying the image data in the selected contiguous sub-region of the display area.

18. The method of claim 17, wherein receiving the command to display content includes receiving a command from a software application, and wherein selecting the appropriate contiguous sub-region is based at least in part on the software application.

19. The method of claim 18, wherein the software application has a priority level associated therewith, and the selection of the appropriate contiguous sub-region of the display area is based at least in part on the priority level.

20. The method of claim 18, wherein selecting the appropriate contiguous sub-region is based at least in part on information relating to the usage history of the software application.

21. The method of claim 17, wherein selecting the appropriate contiguous sub-region is based at least in part on a desired image resolution.

22. The method of claim 17, wherein selecting the appropriate contiguous sub-region is based at least in part on a range of colors to be displayed.

23. The method of claim 17, wherein selecting the appropriate contiguous sub-region is based at least in part on a frame rate at which the image data is to be displayed.

24. The method of claim 17, wherein selecting the appropriate contiguous sub-region is based at least in part on a size and shape of an area in which the image data is to be displayed.

25. The method of claim 17, wherein displaying the content in the selected contiguous sub-region of the wearable display device includes moving the display of content from one of the at least two sub-regions to another of the at least two sub-regions.

26. A wearable display device, comprising:
   a display, the display including a first contiguous region of the display configured to display images at a first image quality and a second contiguous region of the display configured to display images at a second image quality;
   and
   a processor capable of:
      selecting a contiguous region of the display in which image data will be displayed based at least in part on a property of the wearable display device; and displaying the image data in the selected contiguous region of the display.

27. The device of claim 26, wherein the first contiguous display region has a first pixel density and the second contiguous display region has a second pixel density different than the first pixel density, and wherein selecting a contiguous region of the display in which image data will be displayed is based at least in part on a resolution of the image data.

28. The device of claim 26, wherein the first contiguous display region is configured to display image data at a first refresh rate and the second contiguous display region is configured to display image data at a second refresh rate different than the first refresh rate, and wherein selecting a contiguous region of the display in which image data will be displayed is based at least in part on a rate at which the image data will be refreshed.

29. The device of claim 26, wherein the first contiguous display region is capable of displaying a first color gamut and the second contiguous display region is capable of displaying a second color gamut different than the first color gamut, and wherein selecting a contiguous region of the display in which image data will be displayed is based at least in part on a color gamut of the image data.

30. The device of claim 26, wherein selecting the appropriate contiguous sub-region is based at least in part on remaining battery life of the wearable display device.

31. The device of claim 26, additionally comprising at least one sensor configured to provide information regarding the orientations of the first and second display regions, wherein selecting a contiguous region of the display in which image data will be displayed is based at least in part on the orientations of the first and second display regions.

* * * * *